(12) United States Patent
Rancati et al.

(10) Patent No.: US 9,012,644 B2
(45) Date of Patent: Apr. 21, 2015

(54) COMPOUNDS HAVING MUSCARINIC RECEPTOR ANTAGONIST AND BETA2 ADRENERGIC RECEPTOR AGONIST ACTIVITY

(75) Inventors: Fabio Rancati, Parma (IT); Andrea Rizzi, Parma (IT); Ian Linney, Saffron Walden (GB); Wesley Blackaby, Saffron Walden (GB); Chris Knight, Saffron Walden (GB)

(73) Assignee: Chiesi Farmaceutici S.p.A., Parma (IT)

( * ) Notice: Subject to any disclaimer, the term of this patent is extended or adjusted under 35 U.S.C. 154(b) by 378 days.

(21) Appl. No.: 13/492,188

(22) Filed: Jun. 8, 2012

(65) Prior Publication Data
US 2013/0034504 A1     Feb. 7, 2013

(30) Foreign Application Priority Data

Jun. 10, 2011  (EP) .................................. 11169535

(51) Int. Cl.
| | | |
|---|---|---|
| *C07D 453/04* | (2006.01) | |
| *A61K 31/47* | (2006.01) | |
| *C07D 401/12* | (2006.01) | |
| *C07D 409/14* | (2006.01) | |
| *C07D 417/12* | (2006.01) | |

(52) U.S. Cl.
CPC ............ *C07D 401/12* (2013.01); *C07D 409/14* (2013.01); *C07D 417/12* (2013.01)

(58) Field of Classification Search
USPC .......................................... 546/134; 514/312
See application file for complete search history.

(56) References Cited

U.S. PATENT DOCUMENTS

2013/0045169 A1    2/2013   Rancati et al.

FOREIGN PATENT DOCUMENTS

| WO | 00/69468 | 11/2000 |
|---|---|---|
| WO | 2004/074246 | 9/2004 |
| WO | 2004/074812 | 9/2004 |
| WO | 2004/106333 | 12/2004 |
| WO | 2005/051946 | 6/2005 |
| WO | 2005/115467 | 12/2005 |
| WO | 2006/023457 | 3/2006 |
| WO | 2006/023460 | 3/2006 |
| WO | 2010/123766 | 10/2010 |
| WO | 2011/048409 | 4/2011 |

OTHER PUBLICATIONS

U.S. Appl. No. 14/098,662, filed Dec. 6, 2013, Rancati, et al.
U.S. Appl. No. 14/098,735, filed Dec. 6, 2013, Rancati, et al.
Europen Search Report in Application No. 11169535.9, issued Nov. 17, 2011.
Nicholas C. Ray et al, Expert Opinion, vol. 19, No. 1 (2009) pp. 1-12.

*Primary Examiner* — John Mabry
(74) *Attorney, Agent, or Firm* — Oblon, McClelland, Maier & Neustadt, L.L.P.

(57) ABSTRACT

Compounds of formula (I) act both as muscarinic receptor antagonists and beta2 adrenergic receptor agonists and are useful for treating and/or preventing broncho-obstructive and inflammatory diseases.

19 Claims, No Drawings

COMPOUNDS HAVING MUSCARINIC RECEPTOR ANTAGONIST AND BETA2 ADRENERGIC RECEPTOR AGONIST ACTIVITY

CROSS REFERENCES TO RELATED APPLICATIONS

This application claims priority to European Patent Application No. 11169535.9 filed on Jun. 10, 2011, which is incorporated herein by reference in its entirety.

BACKGROUND OF THE INVENTION

1. Field of the Invention

The present invention relates to compounds, which act both as muscarinic receptor antagonists and beta2 adrenergic receptor agonists, to processes for preparing such a compound, to compositions which contain such a compound, to therapeutic uses of such a compound, and combinations of such a compound with other pharmaceutical active ingredients.

2. Discussion of the Background

Pulmonary disorders, such as asthma and chronic obstructive pulmonary disease (COPD), are commonly treated with bronchodilators. A well known class of bronchodilators consists of beta-2 adrenergic receptor agonists, such as salbutamol, fenoterol, formoterol, and salmeterol. These compounds are generally administered by inhalation.

Another well known class of bronchodilators consists of muscarinic receptor antagonists (anticholinergic compounds), such as ipratropium and tiotropium. These compounds are also typically administered by inhalation.

Inhaled formulations of both beta-2 agonists and muscarinic receptor antagonists are valuable agents in the treatment of asthma and COPD, with both classes of agents providing symptomatic relief due to their ability to relax constricted airways. Observations that the bronchodilator effects of the two classes of agents were additive prompted studies with combinations of the of the two agents. In 1975, it was shown that that beneficial effects could be achieved by combining two ingredients such as fenoterol and ipratropium bromide in a single aerosol. This prompted the development of fixed dose combinations of ipratropium bromide firstly with fenoterol (Berodual, introduced in 1980), and then with salbutamol (Combivent, introduced in 1994).

More recently the availability of both long-acting muscarinic antagonists and long-acting beta-2 agonists prompted the development of combinations of these agents. For example, WO 00/69468 (which is incorporated herein by reference in its entirety) discloses medicament compositions containing a muscarinic receptor antagonist, such as tiotropium bromide, and beta-2 adrenergic receptor agonists, such as formoterol fumarate or salmeterol, and WO 2005/115467 (which is incorporated herein by reference in its entirety) discloses a combination which comprises a beta-2 agonist and an antagonist of M3 muscarinic receptors which is a salt of 3(R)-(2-hydroxy-2,2-dithien-2-ylacetoxy)-1-(3-phenoxypropyl)-1-azoniabicyclo[2.2.2]octane.

An alternative approach to the development of fixed dose combinations is the identification of molecules that combine both activities of muscarinic antagonism and beta-2 agonism. In fact compounds possessing both beta-2 adrenergic receptor agonist and muscarinic receptor antagonist activity are highly desirable since such bifunctional compounds would provide bronchodilation through two independent mechanisms of action while having a single molecule pharmacokinetics.

Such kind of compounds have been described in some patent applications, such as WO 2004/074246, WO 2004/074812, WO 2005/051946, WO 2006/023457, WO 2006/023460, WO 2010/123766, and WO 2011/048409 (which are incorporated herein by reference in their entireties).

However, there remains a need for compounds which exhibit both muscarinic antagonism and beta-2 agonism.

SUMMARY OF THE INVENTION

Accordingly, it is one object of the present invention to provide novel compounds, which act both as muscarinic receptor antagonists and beta2 adrenergic receptor agonists.

It is another object of the present invention to provide novel processes for preparing such a compound.

It is another object of the present invention to provide novel compositions which contain such a compound, to therapeutic uses of such a compound, and combinations of such a compound with other pharmaceutical active ingredients.

It is another object of the present invention to provide novel therapeutic uses of such a compound, and combinations of such a compound with other pharmaceutical active ingredients.

It is another object of the present invention to provide novel combinations of such a compound with other pharmaceutical active ingredients.

These and other objects, which will become apparent during the following detailed description, have been achieved by the inventors' discovery that compounds of general formula (I) act both as muscarinic receptor antagonists and beta2 adrenergic receptor agonists.

Thus, in a first embodiment, the present invention provides compounds of formula (I) and pharmaceutically acceptable salts thereof.

In a second embodiment, the present invention provides processes for preparing such a compound or salt.

In another embodiment, the present invention provides, compositions which contain such a compound or salt.

In another embodiment, the present invention provides, therapeutic uses of such a compound or salt.

In another embodiment, the present invention provides combinations of such a compound or salt with another pharmaceutical active ingredient among which are, for instance, those currently used in the treatment of respiratory disorders, e.g. corticosteroids, P38 MAP kinase inhibitors, IKK2, FINE inhibitors, PDE4 inhibitors, leukotriene modulators, NSAIDs and mucus regulators.

It has now been found that some particular ester or thioester derivatives, besides possessing both beta-2 adrenergic receptor agonist and muscarinic receptor antagonist activity, possess elevated affinity for the M3 muscarinic receptors and long lasting bronchodilating activity.

DETAILED DESCRIPTION OF THE PREFERRED EMBODIMENTS

In particular, the present invention is directed to compounds of general formula (I):

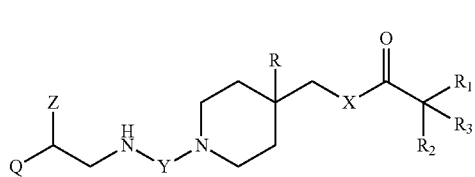
(I)

wherein

Q is a group of formula Q1, Q2, Q3, Q4, Q5 or Q6:

Q1

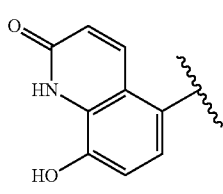

Q2

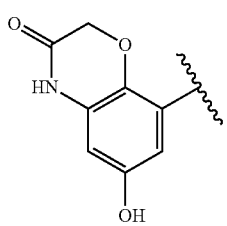

Q3

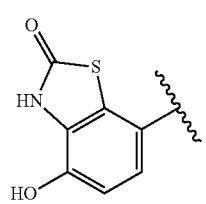

Q4

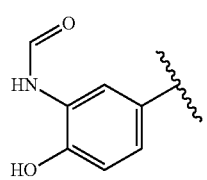

Q5

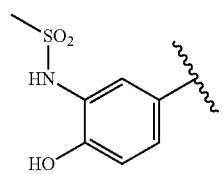

Q6

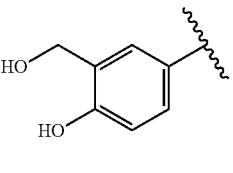

Z is H or OH;

Y is —$(CH_2)_n$— wherein n is an integer between 1 and 12 or is a divalent group of formula Y1

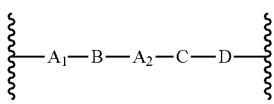
Y1 wherein

A1 and A2 are, each independently, absent or are selected from the group consisting of $(C_1-C_6)$alkylene, $(C_3-C_8)$cycloalkylene and $(C_3-C_8)$heterocycloalkylene;

B is absent or is selected from the group consisting of $(C_3-C_8)$cycloalkylene, $(C_3-C_8)$heterocycloalkylene, arylene, and heteroarylene or is a group of formula B1

B1

[indane structure]

C is absent or is selected from the group consisting of —O—, —OCO—, —C(O)O—, —S—, —S(O)—, —S(O)$_2$— and —N(R$_4$)— or is one of the following groups C1-C10

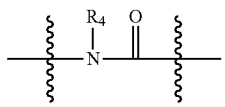
C1

C2

C3

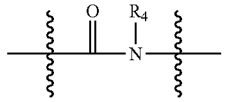
C4

C5

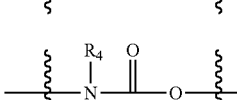
C6

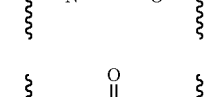
C7

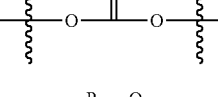
C8

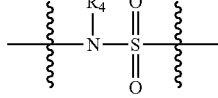

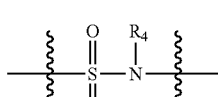

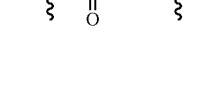

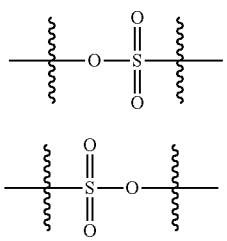

wherein R$_4$ is H or is selected from the group consisting of (C$_1$-C$_8$)alkyl, (C$_3$-C$_8$)cycloalkyl, (C$_3$-C$_8$)heterocycloalkyl, aryl, and heteroaryl;

D is selected from the group consisting of (C$_1$-C$_{12}$)alkylene, (C$_2$-C$_{12}$)alkenylene, and (C$_2$-C$_6$)alkynylene, optionally substituted by one or more (C$_1$-C$_6$)alkyl;

R is —H or (C$_1$-C$_4$)alkyl;

X is —O— or —S—;

R$_1$ is H or is selected from the group consisting of (C$_3$-C$_8$) cycloalkyl, aryl, heteroaryl, aryl(C$_1$-C$_6$)alkyl, heteroaryl(C$_1$-C$_6$)alkyl, and (C$_3$-C$_8$)cycloalkyl(C$_1$-C$_6$)alkyl, optionally substituted by one or more (C$_1$-C$_4$)alkoxy;

R$_2$ is selected from the group consisting of (C$_3$-C$_8$)cycloalkyl, aryl, heteroaryl, aryl(C$_1$-C$_6$)alkyl, heteroaryl(C$_1$-C$_6$)alkyl, and (C$_3$-C$_8$)cycloalkyl(C$_1$-C$_6$)alkyl, optionally substituted by one or more halogen atoms or (C$_1$-C$_4$)alkoxy;

R$_3$ is H or is selected from the group consisting of —OH, hydroxy(C$_1$-C$_6$)alkyl, —N(R$_5$R$_6$) and —N(R$_5$)CO(R$_6$);

R$_5$ and R$_6$ are independently H or (C$_1$-C$_6$)alkyl;

and pharmaceutically acceptable salts or solvates thereof.

The expression "(C$_1$-C$_6$)alkyl" refers to straight or branched chain alkyl groups, wherein the number of carbon atoms is from 1 to 6. Examples of groups are methyl, ethyl, n-propyl, isopropyl, t-butyl, pentyl, hexyl, and the like.

In an analogous manner, the expression "(C$_1$-C$_x$)alkylene" refers to divalent groups, wherein the number of carbon atoms is from 1 to x, such as methylene, ethylene, n-propylene, isopropylene, t-butylene, pentylene, hexylene, octylene, nonylene, decylene, undecylene, dodecylene, and the like.

The expression "hydroxy(C$_1$-C$_6$)alkyl" refers to -alkyl- substituted by hydroxyl groups.

The expression "(C$_2$-C$_6$)alkenyl" refers to straight or branched carbon chains with one or more double bonds, wherein the number of carbon atoms is from 2 to 6. Examples of said groups include ethenyl, propenyl, butenyl, pentenyl, hexenyl, and the like.

In an analogous manner, the expression "(C$_2$-C$_x$)alkenylene" refers to divalent groups, wherein the number of carbon atoms is from 2 to x, such as ethenylene, propenylene, butenylene, pentenylene, hexenylene, heptenylene, octenylene, nonenylene, decenylene, undecenylene, dodecenylene, and the like.

The expression "(C$_2$-C$_6$)alkynyl" refers to straight or branched carbon chains with one or more triple bonds, wherein the number of carbon atoms is from 2 to 6. Examples of said groups include ethynyl, propynyl, butynyl, pentynyl, hexynyl, and the like.

In an analogous manner, the expression "(C$_2$-C$_x$)alkynylene" refers to divalent groups, wherein the number of carbon atoms is from 2 to x, such as ethynylene, propynylene, butynylene, pentynylene, hexynylene, and the like.

The expression "(C$_1$-C$_6$)alkoxy" refers to alkyl-oxy (e.g. alkoxy) groups, with the alkyl portion as above defined. Examples of said groups include methoxy, ethoxy, n-propoxy, isopropoxy, n-butoxy, isobutoxy, sec-butoxy, tert-butoxy, pentoxy, hexoxy, and the like.

The expression "(C$_3$-C$_8$)cycloalkyl" refers to mono- or bi-cycloaliphatic hydrocarbon groups with 3 to 8 carbon atoms. Examples include cyclopropyl, cyclobutyl, cyclopentyl, cyclohexyl, cycloheptyl, bicyclo[2.2.1]hept-2-yl, and the like.

The expression "(C$_3$-C$_8$)heterocycloalkyl" refers to (C$_3$-C$_8$)cycloalkyl groups, in which at least one ring carbon atom is replaced by a heteroatom or heteroaromatic group (e.g. N, NH, S or O). Examples include quinuclidinyl, pyrrolidinyl, piperidinyl, and the like.

In an analogous manner, the expressions "(C$_3$-C$_8$)cycloalkylene" and "(C$_3$-C$_8$)heterocycloalkylene" refer to divalent groups, such as, respectively, cyclopropylene, cyclobutylene, cyclopentylene, cyclohexylene, cycloheptylene, bicyclo[2.2.1]hept-2-ylene and quinuclidinylene, pyrrolidinylene, piperidinylene, azabicyclo[3.2.1]octan-3-ylene and azoniabicyclo[2.2.2]octanylene.

The expression "aryl" refers to mono, bi- or tricyclic ring systems having 5 to 20, preferably 5 to 15, ring atoms, and wherein at least one ring is aromatic.

The expression "heteroaryl" refers to mono, bi- or tricyclic ring systems with 5 to 20 ring atoms, preferably 5 to 15, in which at least one ring is aromatic and in which at least one carbon ring atom is a heteroatom or heteroaromatic group (e.g. N, NH, S or O).

Examples of suitable aryl or heteroaryl monocyclic systems include, for instance, thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolidinyl), furan (furanyl) radicals, and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydrobenzo dioxepin, benzo oxazin radicals, and the like.

Examples of suitable aryl or heteroaryl tricyclic systems include fluorene radicals as well as benzocondensed derivatives of the aforementioned heteroaryl bicyclic systems.

In an analogous manner, the expressions "arylene" and "heteroarylene" refer to divalent groups, such as phenylene and thienylene.

The expressions "aryl(C$_1$-C$_6$)alkyl", "heteroaryl(C$_1$-C$_6$)alkyl" and "(C$_3$-C$_8$)cycloalkyl(C$_1$-C$_6$)alkyl" refer to a "(C$_1$-C$_6$)alkyl" respectively substituted by one or more aryl, heteroaryl, or (C$_3$-C$_8$)cycloalkyl groups as defined above.

Examples of aryl(C$_1$-C$_6$)alkyl include benzyl, triphenylmethyl, and the like.

Whenever basic amino groups are present in the compounds of formula (I), physiological acceptable anions, selected among chloride, bromide, fluoride, iodide, trifluoroacetate, formate, sulfate, phosphate, methanesulfonate, nitrate, maleate, acetate, citrate, fumarate, tartrate, oxalate, succinate, benzoate, and p-toluenesulfonate, may be present. Likewise, in the presence of acidic groups such as COOH groups, corresponding physiological cation salts may be present as well, for instance including alkaline, alkaline earth metal ions, or ammonium salts.

It will be apparent that the compounds of general formula (I) may contain asymmetric centers. Therefore, the invention also includes any of the optical stereoisomers, diastereoisomers, and mixtures thereof, in any proportion.

In particular, the carbon atom linked to $R_1$, $R_2$ and $R_3$ groups, depending on the meanings provided to $R_1$, $R_2$ and $R_3$ among those formerly reported, may represent a chiral center.

In a first preferred embodiment, the absolute configuration of this chiral center may be (R).

In another embodiment the preferred configuration is (S).

In a preferred embodiment, the compounds of general formula (I) described in the present invention are present as mixtures of diastereoisomers.

In another embodiment, when in the compounds of general formula (I) Z is —OH, the carbon atom linked to Q and Z represents a chiral center, wherein (R) is the preferred configuration.

A first preferred group of compounds is that of general formula (I) wherein $R_1$ is H or is selected from the group consisting of ($C_3$-$C_8$)cycloalkyl, aryl, heteroaryl, and aryl($C_1$-$C_6$)alkyl; $R_2$ is selected from the group consisting of ($C_3$-$C_8$)cycloalkyl, aryl, heteroaryl, aryl($C_1$-$C_6$)alkyl, heteroaryl($C_1$-$C_6$)alkyl, and ($C_3$-$C_8$)cycloalkyl($C_1$-$C_6$)alkyl; $R_3$ is H or is selected from the group consisting of —OH, hydroxy($C_1$-$C_6$)alkyl, —N($R_5R_6$), and —N($R_5$)CO($R_6$); X is —O— or —S—; R is —H or ($C_1$-$C_4$)alkyl; and Y, Z and Q are as defined above.

Still more preferred within this class are the compounds of general formula (I) wherein $R_1$ is H or is selected from the group consisting of cyclobutyl, cyclopentyl, phenyl, benzyl, cycloheptyl, thienyl, and cyclohexyl; $R_2$ is selected from the group consisting of phenyl, thienyl, cyclohexyl, triphenylmethyl, chlorophenyl, methoxyphenyl and fluorophenyl; $R_3$ is H or is selected from the group consisting of —OH, —NH$_2$, —CH$_2$OH, and —NHCOCH$_3$; X is —O—; and R is H or —CH$_3$.

A second preferred group of compounds of general formula (I) is that wherein $R_1$, $R_2$, $R_3$, X and R are as defined above; Y is —(CH$_2$)$_n$— wherein n is an integer between 1 and 12 or is a group of formula Y1

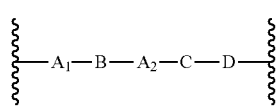

wherein

A1 and A2 are, each independently, absent or are selected from the group consisting of ($C_1$-$C_6$)alkylene, ($C_3$-$C_8$)cycloalkylene, and ($C_3$-$C_8$)heterocycloalkylene; B is absent or is selected from the group consisting of ($C_3$-$C_8$)cycloalkylene, ($C_3$-$C_8$)heterocycloalkylene, arylene, and heteroarylene or is a group of formula B1

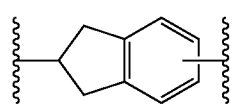

C is absent or is selected from the group consisting of —O—, —OCO—, —C(O)O—, —S—, —N($R_4$)— or is one of the following C1-C10 groups

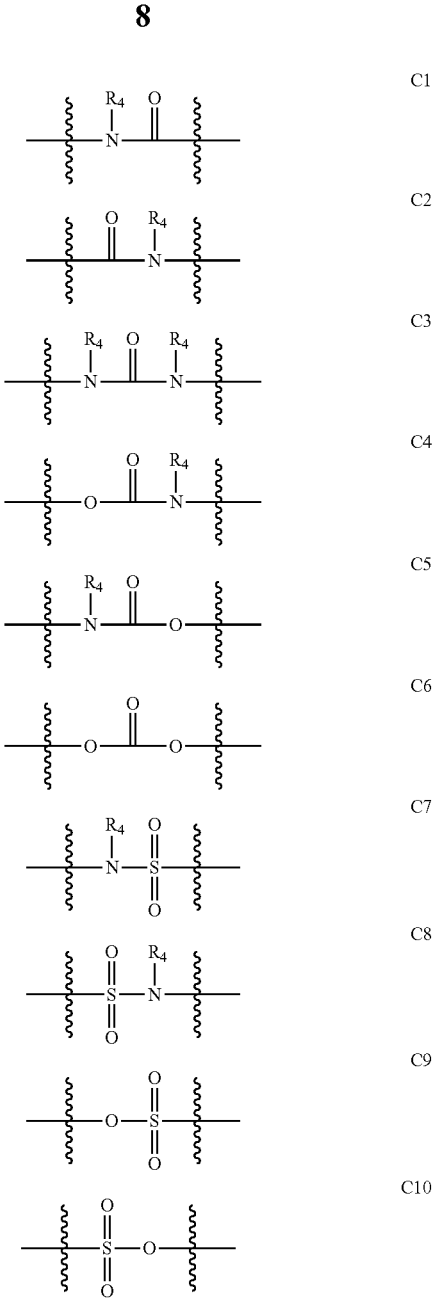

wherein $R_4$ is H or is selected from the group consisting of ($C_1$-$C_8$)alkyl, ($C_3$-$C_8$)cycloalkyl, ($C_3$-$C_8$)heterocycloalkyl, aryl and heteroaryl; D is selected from the group consisting of ($C_1$-$C_{12}$)alkylene, ($C_2$-$C_{12}$)alkenylene, and ($C_2$-$C_6$)alkynylene, optionally substituted by one or more ($C_1$-$C_6$)alkyl;

Z is —H or —OH and Q is a group of formula Q1, Q2, Q3, Q4, Q5 or Q6

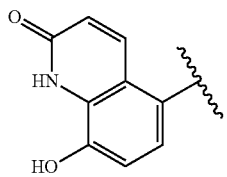

-continued

Q2
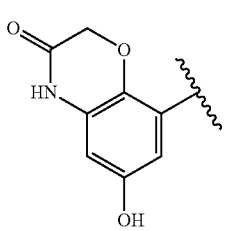

Q3
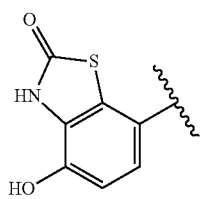

Q4
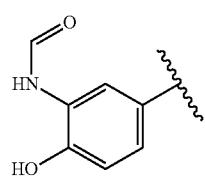

Q5
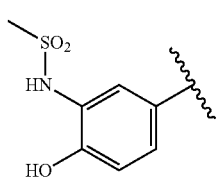

Q6
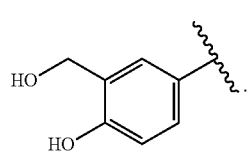

Still more preferred within this class, are the compounds of general formula (I), wherein Y is —(CH$_2$)$_n$—, Z is OH and Q is a group of formula Q1

Q1
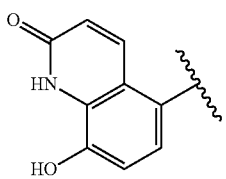

according to general formula (IA)

(IA)
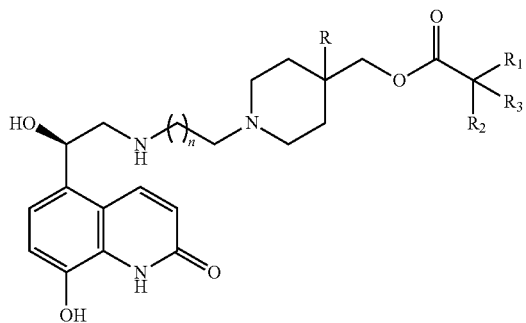

Even still more preferred are the compounds of general formula (IA) wherein n is 4, 5, 6, 7, or 8.

Another class of preferred compounds of general formula (I) is that wherein Y is a divalent group of formula Y1

Y1
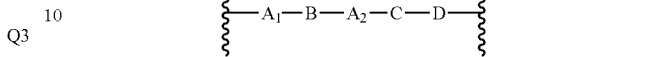

wherein A1 is (C$_3$-C$_8$)cycloalkylene, B and C are absent, D is (C$_1$-C$_{12}$)alkylene, Z is OH and Q is a group of formula Q1

Q1
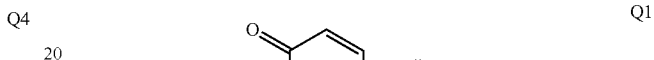

according to general formula (IB), wherein (C$_3$-C$_8$)cycloalkylene is represented by "cy"

(IB)

Even still more preferred are the compounds of general formula (I) wherein Y is a divalent group of formula Y1 wherein A1 is piperinyl, D is hexylene, Z is OH and Q is a group of formula Q1

Q1
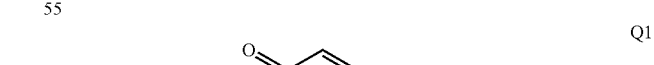

Another preferred class is represented by the compounds of general formula (I), wherein Y is —(CH$_2$)$_n$—, Z is H and Q is a group of formula Q3

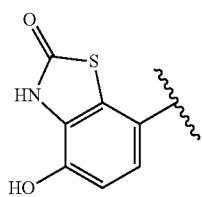

according to general formula (IC)

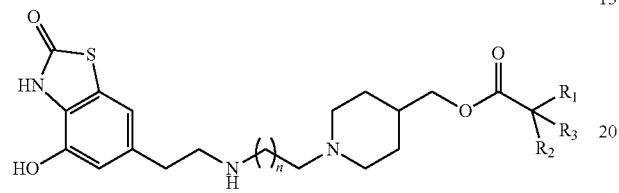

(IC)

Even still more preferred are the compounds of general formula (IC) wherein n is 8.

It is to be understood that all preferred groups or embodiments described above for compounds of formula (I) may be combined among each other and apply to compounds of formula (IA), (IB) and (IC) as well, mutatis mutandis.

The present invention also provides pharmaceutical compositions of the compounds of formula (I) alone or in combination with or in admixture with one or more pharmaceutically acceptable carriers and/or excipients.

The present invention also provides the use of compounds of formula (I) for preparing a medicament.

In a further aspect, the invention provides the use of compounds of formula (I) for the prevention and/or treatment of any broncho-obstructive or inflammatory disease, preferably asthma or chronic bronchitis or chronic obstructive pulmonary disease (COPD).

In a further aspect, the invention provides the use of compounds of formula (I) for the manufacture of a medicament for the prevention and/or treatment of any broncho-obstructive or inflammatory disease, preferably asthma or chronic bronchitis or chronic obstructive pulmonary disease (COPD).

The present invention further provides a method for prevention and/or treatment of any broncho-obstructive or inflammatory disease, preferably asthma or chronic bronchitis or chronic obstructive pulmonary disease (COPD), which comprises administering to a subject in need thereof a therapeutically effective amount of a compound of general formula (I).

The present invention also provides pharmaceutical compositions suitable for administration by inhalation.

Inhalable preparations include inhalable powders, propellant-containing metering aerosols or propellant-free inhalable formulations.

The invention is also directed to devices which may be a single- or multi-dose dry powder inhaler, a metered dose inhaler and a soft mist nebulizer comprising the compounds of formula (I).

The invention is also directed to kits comprising a pharmaceutical composition of a compound of formula (I) alone or in combination with or in admixture with one or more pharmaceutically acceptable carriers and/or excipients and a device which may be a single- or multi-dose dry powder inhaler, a metered dose inhaler and a soft mist nebulizer comprising the compounds of general formula (I).

The present invention is also directed to a process for the preparation of compounds of general formula (I), which process comprises the reaction of intermediate 7

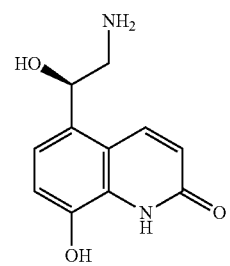

with a compound of general formula 6

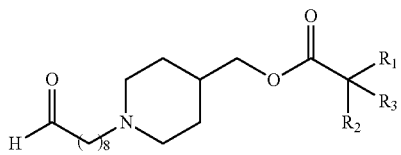

wherein $R_1$, $R_2$ and $R_3$ have the meanings reported above.

The present invention is also directed to a process for the preparation of compounds of general formula (I), which comprises the alkylation of compound of formula 7 with a compound of general formula 8

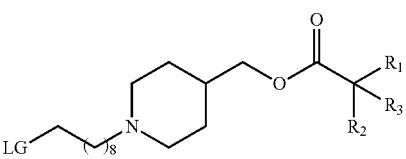

wherein LG is a leaving group suitable to react with an amine.

According to specific embodiments, the present invention provides the compounds reported below:

| Compound | Chemical name |
|---|---|
| 1 | (1-(9-((R)-2-hydroxy-2-(8-hydroxy-2-oxo-1,2-dihydroquinolin-5-yl)ethylamino)nonyl)piperidin-4-yl)methyl 2-cyclohexyl-2-hydroxy-2-phenylacetate |
| 2 | (1-(9-((R)-2-hydroxy-2-(8-hydroxy-2-oxo-1,2-dihydroquinolin-5-yl)ethylamino)nonyl)piperidin-4-yl)methyl 2-cyclobutyl-2-hydroxy-2-phenylacetate |

| Compound | Chemical name |
|---|---|
| 3 | (1-(9-((R)-2-hydroxy-2-(8-hydroxy-2-oxo-1,2-dihydroquinolin-5-yl)ethylamino)nonyl)piperidin-4-yl)methyl 2-cyclopentyl-2-hydroxy-2-phenylacetate |
| 4 | (R)-(1-(9-(2-hydroxy-2-(8-hydroxy-2-oxo-1,2-dihydroquinolin-5-yl)ethylamino)nonyl)piperidin-4-yl)methyl 2-hydroxy-2,2-diphenylacetate |
| 5 | (1-(9-((R)-2-hydroxy-2-(8-hydroxy-2-oxo-1,2-dihydroquinolin-5-yl)ethylamino)nonyl)piperidin-4-yl)methyl 2-hydroxy-2,3-diphenylpropanoate |
| 6 | (1-(9-((R)-2-hydroxy-2-(8-hydroxy-2-oxo-1,2-dihydroquinolin-5-yl)ethylamino)nonyl)piperidin-4-yl)methyl 2-cycloheptyl-2-hydroxy-2-phenylacetate |
| 7 | (R)-(1-(9-((R)-2-hydroxy-2-(8-hydroxy-2-oxo-1,2-dihydroquinolin-5-yl)ethylamino)nonyl)-4-methylpiperidin-4-yl)methyl 2-cyclohexyl-2-hydroxy-2-phenylacetate |
| 8 | (1-(9-((R)-2-hydroxy-2-(8-hydroxy-2-oxo-1,2-dihydroquinolin-5-yl)ethylamino)nonyl)piperidin-4-yl)methyl 2-cyclohexyl-2-phenylacetate |
| 9 | (1-(9-((R)-2-hydroxy-2-(8-hydroxy-2-oxo-1,2-dihydroquinolin-5-yl)ethylamino)nonyl)piperidin-4-yl)methyl 2-cyclohexyl-2-hydroxy-2-(thiophen-2-yl)acetate |
| 10 | (1-(9-((R)-2-hydroxy-2-(8-hydroxy-2-oxo-1,2-dihydroquinolin-5-yl)ethylamino)nonyl)piperidin-4-yl)methyl 2-hydroxy-2-phenyl-2-(thiophen-3-yl)acetate |
| 11 | (R)-(1-(9-(2-hydroxy-2-(8-hydroxy-2-oxo-1,2-dihydroquinolin-5-yl)ethylamino)nonyl)piperidin-4-yl)methyl 2-amino-2,2-diphenylacetate |
| 12 | (R)-(1-(9-(2-hydroxy-2-(8-hydroxy-2-oxo-1,2-dihydroquinolin-5-yl)ethylamino)nonyl)piperidin-4-yl)methyl 2-hydroxy-2,2-di(thiophen-2-yl)acetate |
| 13 | (S)-(1-(9-((R)-2-hydroxy-2-(8-hydroxy-2-oxo-1,2-dihydroquinolin-5-yl)ethylamino)nonyl)piperidin-4-yl)methyl 2-cyclohexyl-2-hydroxy-2-phenylacetate |
| 14 | (R)-(1-(9-((R)-2-hydroxy-2-(8-hydroxy-2-oxo-1,2-dihydroquinolin-5-yl)ethylamino)nonyl)piperidin-4-yl)methyl 2-cyclohexyl-2-hydroxy-2-phenylacetate |
| 15 | (1-(9-((R)-2-hydroxy-2-(8-hydroxy-2-oxo-1,2-dihydroquinolin-5-yl)ethylamino)nonyl)piperidin-4-yl)methyl 2-hydroxy-2-phenyl-2-(thiophen-2-yl)acetate |
| 16 | (1-(8-((R)-2-hydroxy-2-(8-hydroxy-2-oxo-1,2-dihydroquinolin-5-yl)ethylamino)octyl)piperidin-4-yl)methyl 2-cyclohexyl-2-hydroxy-2-phenylacetate |
| 17 | (1-(7-((R)-2-hydroxy-2-(8-hydroxy-2-oxo-1,2-dihydroquinolin-5-yl)ethylamino)heptyl)piperidin-4-yl)methyl 2-cyclohexyl-2-hydroxy-2-phenylacetate |
| 18 | (1-(5-((R)-2-hydroxy-2-(8-hydroxy-2-oxo-1,2-dihydroquinolin-5-yl)ethylamino)pentyl)piperidin-4-yl)methyl 2-cyclohexyl-2-hydroxy-2-phenylacetate |
| 19 | (1-(6-((R)-2-hydroxy-2-(8-hydroxy-2-oxo-1,2-dihydroquinolin-5-yl)ethylamino)hexyl)piperidin-4-yl)methyl 2-cyclohexyl-2-hydroxy-2-phenylacetate |
| 20 | (R)-(1-(9-(2-hydroxy-2-(8-hydroxy-2-oxo-1,2-dihydroquinolin-5-yl)ethylamino)nonyl)piperidin-4-yl)methyl 3-hydroxy-2,2-diphenylpropanoate |
| 21 | (R)-(1-(9-(2-hydroxy-2-(8-hydroxy-2-oxo-1,2-dihydroquinolin-5-yl)ethylamino)nonyl)piperidin-4-yl)methyl 2,2-dicyclohexyl-2-hydroxyacetate |
| 22 | (R)-(1-(9-(2-hydroxy-2-(8-hydroxy-2-oxo-1,2-dihydroquinolin-5-yl)ethylamino)nonyl)piperidin-4-yl)methyl 3,3,3-triphenylpropanoate |
| 23 | (R)-(1-(9-(2-hydroxy-2-(8-hydroxy-2-oxo-1,2-dihydroquinolin-5-yl)ethylamino)nonyl)piperidin-4-yl)methyl 2-acetamido-2,2-diphenylacetate |
| 24 | (1-(9-((R)-2-hydroxy-2-(8-hydroxy-2-oxo-1,2-dihydroquinolin-5-yl)ethylamino)nonyl)piperidin-4-yl)methyl 2-(4-chlorophenyl)-2-hydroxy-2-phenylacetate |
| 25 | (1-(9-((R)-2-hydroxy-2-(8-hydroxy-2-oxo-1,2-dihydroquinolin-5-yl)ethylamino)nonyl)piperidin-4-yl)methyl 2-cyclohexyl-2-hydroxy-2-(thiophen-3-yl)acetate |
| 26 | (1-(9-((R)-2-hydroxy-2-(8-hydroxy-2-oxo-1,2-dihydroquinolin-5-yl)ethylamino)nonyl)piperidin-4-yl)methyl 2-hydroxy-2-(3-methoxyphenyl)-2-phenylacetate |
| 27 | (1-(9-((R)-2-hydroxy-2-(8-hydroxy-2-oxo-1,2-dihydroquinolin-5-yl)ethylamino)nonyl)piperidin-4-yl)methyl 2-(4-fluorophenyl)-2-hydroxy-2-phenylacetate |
| 28 | (1-(6-(4-((R)-2-hydroxy-2-(8-hydroxy-2-oxo-1,2-dihydroquinolin-5-yl)ethylamino)piperidin-1-yl)hexyl)piperidin-4-yl)methyl 2-cyclohexyl-2-hydroxy-2-phenylacetate |

| Compound | Chemical name |
|---|---|
| 29 | (1-(9-(2-(4-hydroxy-2-oxo-2,3-dihydrobenzo[d]thiazol-7-yl)ethylamino)nonyl)piperidin-4-yl)methyl 2-cyclohexyl-2-hydroxy-2-phenylacetate |
| 30 | (1-((E)-5-(3-(((R)-2-hydroxy-2-(8-hydroxy-2-oxo-1,2-dihydroquinolin-5-yl)ethyl)amino)propoxy)-4-methylpent-3-en-1-yl)piperidin-4-yl)methyl 2-cyclohexyl-2-hydroxy-2-phenylacetate |
| 31 | (R)-(1-(4-((6-((2-hydroxy-2-(8-hydroxy-2-oxo-1,2-dihydroquinolin-5-yl)ethyl)amino)hexyl)oxy)benzyl)piperidin-4-yl)methyl 2-hydroxy-2,2-diphenylacetate |
| 32 | (R)-(1-(4-((6-((2-hydroxy-2-(8-hydroxy-2-oxo-1,2-dihydroquinolin-5-yl)ethyl)amino)butyl)oxy)benzyl)piperidin-4-yl)methyl 2-hydroxy-2,2-diphenylacetate |
| 33 | (R)-(1-(4-((6-((2-hydroxy-2-(8-hydroxy-2-oxo-1,2-dihydroquinolin-5-yl)ethyl)amino)pentyl)oxy)benzyl)piperidin-4-yl)methyl 2-hydroxy-2,2-diphenylacetate |
| 34 | (1-(4-((6-(((R)-2-hydroxy-2-(8-hydroxy-2-oxo-1,2-dihydroquinolin-5-yl)ethyl)amino)hexyl)oxy)benzyl)piperidin-4-yl)methyl 2-cyclohexyl-2-hydroxy-2-phenylacetate |
| 35 | (1-(4-((6-(((R)-2-hydroxy-2-(8-hydroxy-2-oxo-1,2-dihydroquinolin-5-yl)ethyl)amino)butyl)oxy)benzyl)piperidin-4-yl)methyl 2-cyclohexyl-2-hydroxy-2-phenylacetate |
| 36 | (1-(4-((6-(((R)-2-hydroxy-2-(8-hydroxy-2-oxo-1,2-dihydroquinolin-5-yl)ethyl)amino)pentyl)oxy)benzyl)piperidin-4-yl)methyl 2-cyclohexyl-2-hydroxy-2-phenylacetate |
| 37 | (R)-(1-(4-((5-((2-hydroxy-2-(8-hydroxy-2-oxo-1,2-dihydroquinolin-5-yl)ethyl)amino)pentyl)oxy)phenethyl)piperidin-4-yl)methyl 2-hydroxy-2,2-diphenylacetate |

The compounds of the present invention can be prepared from readily available starting materials using the following known general methods and procedures or by using other readily available methods known in the art. Although a particular embodiment of the present invention may be shown or described herein, those skilled in the art will recognize that all embodiments or aspects of the present invention can be prepared using the methods described herein or by using other known methods, reagents and starting materials. It will also be appreciated that where typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by one skilled in the art by routine optimisation procedures.

Compounds of general formula (I) may be prepared according to the following synthetic Scheme, wherein Bn stands for benzyl group.

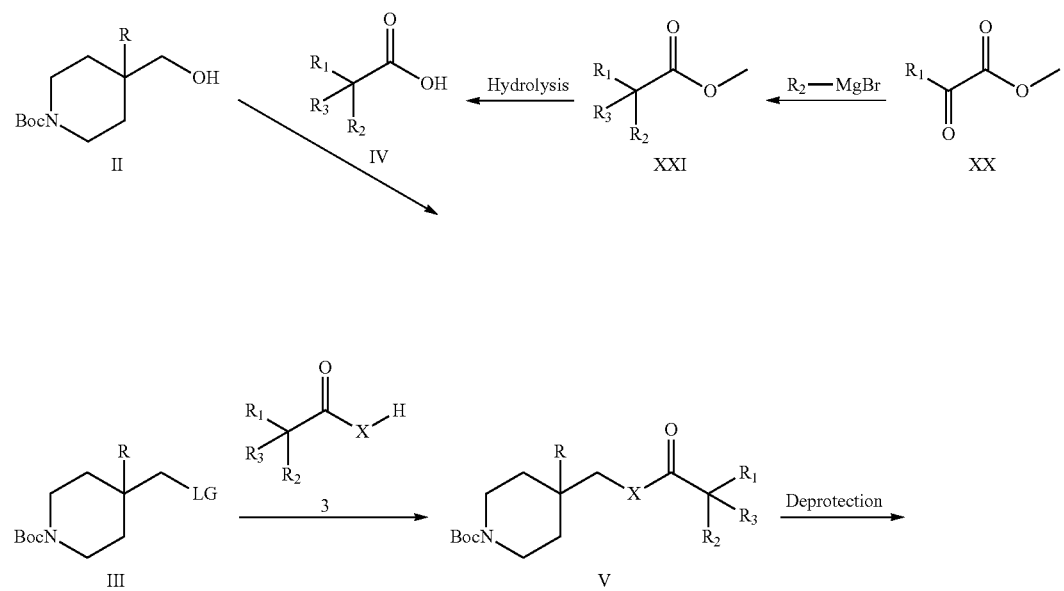

-continued
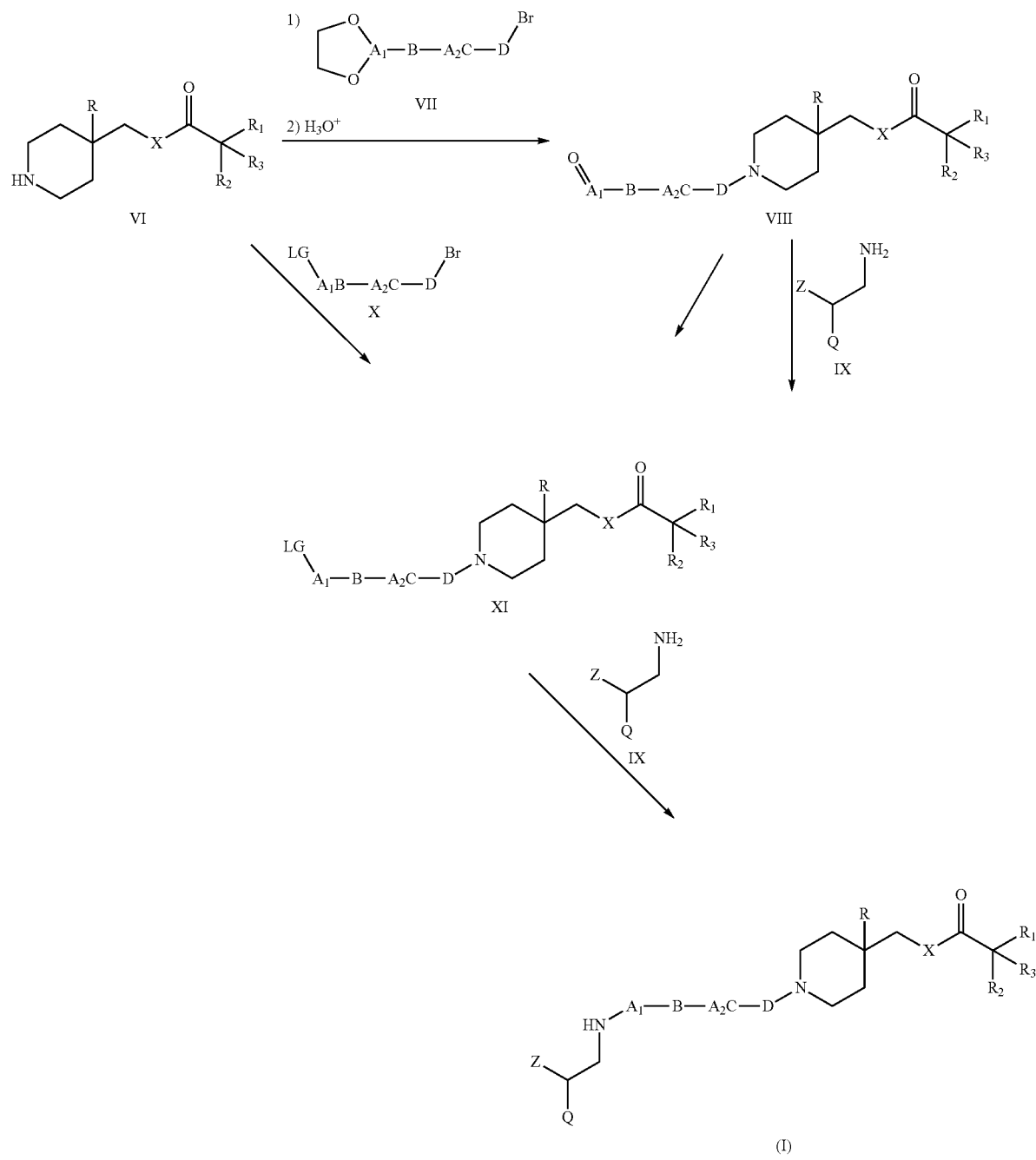
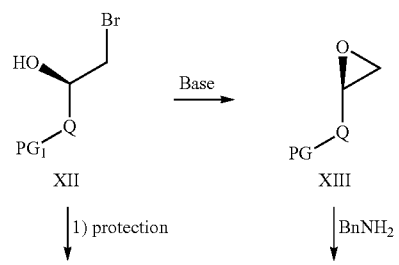

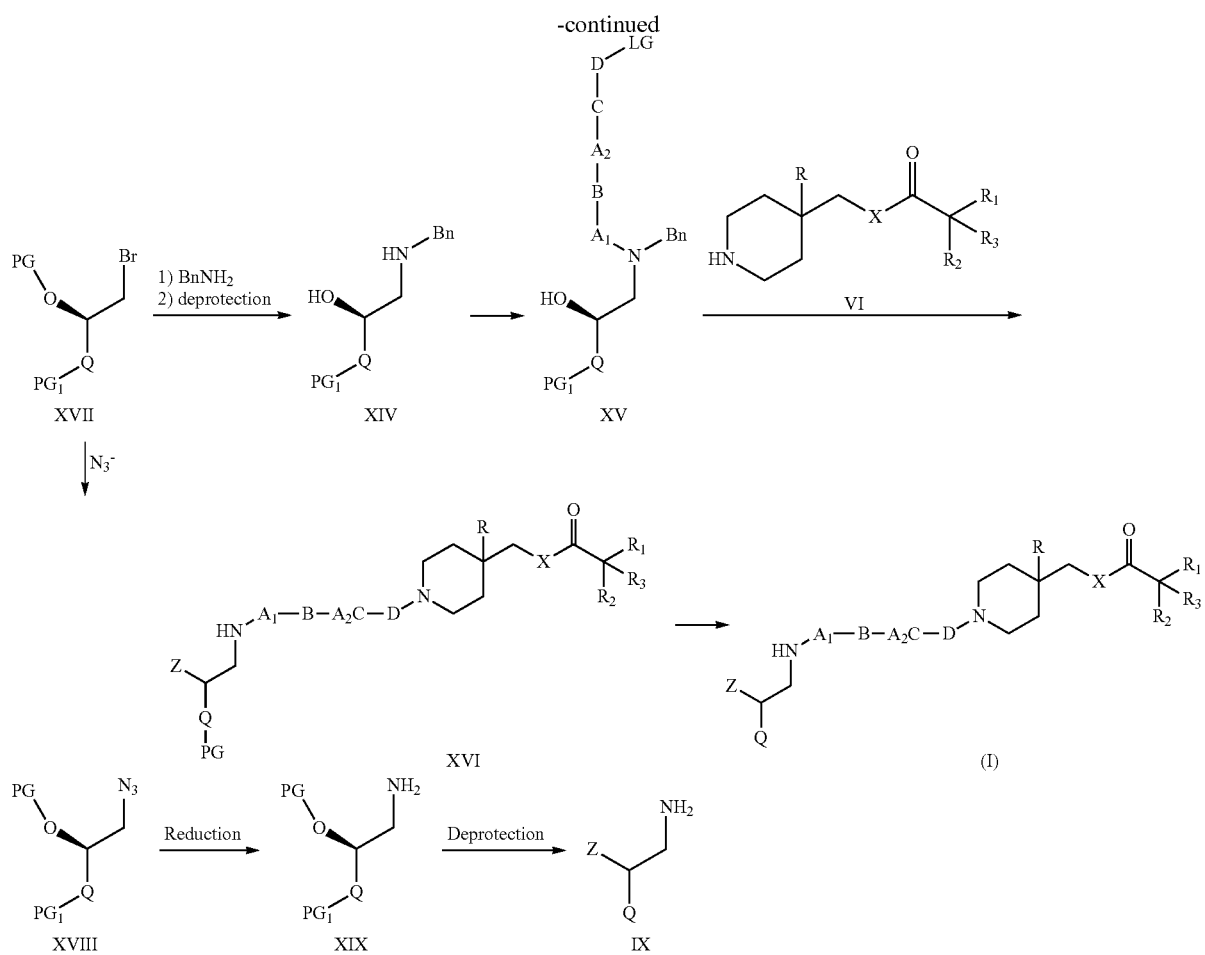

General Procedure for the Preparation of Compounds of Formula (I)

Compounds of general formula (I) can be prepared with several different methods, some of those are reported in Scheme, which applies for example for the preparation of a compound of general formula (I) wherein Y is a group of formula Y1 and wherein A1 is ($C_1$-$C_6$)alkylene, A2, B and C are absent and D is ($C_1$-$C_6$)alkylene. This is just a non-limiting example. A similar approach can be used for the preparation of compounds of general formula (I) wherein A1, A2, B, C and D have the meanings reported above applying the well known methodologies described in the literature for the introduction of specific moieties in organic compounds.

The compounds of general formula VII indicate a compound wherein A1 is ($C_1$-$C_6$)alkylene, cycloalkylene, or heterocycloalkylene substituted with oxo, leading to an aldehyde or ketone protected as cyclic acetal. This cyclic acetal protecting group can be removed leading to a compound of general formula VIII. In the case A1 is absent and B is a cycloalkylene, heterocycloalkylene, or a group of formula B1, the carbonyl moiety, as such or protected, must be considered on group B.

The synthesis of compounds of general formula (I) may require the protection of potential reactive functionality in addition to those methods already described. In such a case, examples of compatible protecting groups and their particular methods of protection and deprotection are described in "Protective Groups in Organic Synthesis" by T. W. Green and P. Wutz (Wiley-Interscience publication, 1999, which is incorporated herein by reference in its entirety).

Compounds of general formula (I) wherein Y is —($CH_2$)$_9$—, can be prepared by reacting an intermediate of formula IX with the aldehyde of formula VIII (wherein R, $R_1$, $R_2$, $R_3$, A1, A2 B, C, D, Z, and Q have the meanings reported above) under the reductive amination conditions. The reaction can be performed in a solvent such as methanol, ethanol, tetrahydrofuran (THF), or dichloromethane (DCM). The reaction protocol depends on the reducing agent used. For example, $NaBH_4$ requires the preliminary formation of the imine, while $NaBCNH_3$ at pH≈5, or $NaAc_3BH$ can be used in a one-pot reaction. In all cases the reaction is completed in a time of from 1 to 12 hours at room temperature (RT).

Intermediates of formula VIII can be easily prepared by alkylation of intermediates of formula VI with a suitable protected aldehyde followed by deprotection. The alkylation reaction occurs in a polar aprotic solvent such as acetonitrile or dimethylformamide (DMF), at temperatures ranging from RT to 100° C. and is completed in 1 to 24 hours. Traditional thermal or microwaves heating can be used to activate the reaction.

Alternatively, compounds of general formula (I) can be obtained via alkylation of intermediates of formula IX with compounds of formula XI, wherein the leaving group (LG) can be chlorine, bromine, mesyl, tosyl, or another known leaving group suitable to react with an amine. The reaction occurs in a solvent such as DCM, THF, acetonitrile, or DMF at RT or higher temperature and is completed, in the presence of an organic or inorganic base, over a period of time between 0.5 to 12 hours.

Intermediates of formula XI can be obtained from compounds of formula VIII via reduction of aldehyde followed by conversion of the obtained alcohol into compounds of formula XI with toluene sulfonyl chloride, methane sulfonyl chloride, $CBr_4$ and $PPh_3$ or $SOCl_2$. All reactions must be performed in an aprotic solvent such as DCM or THF. Intermediates of formula XI can be obtained by alkylation of a compound of formula VI with a bifunctional reagent of formula X such as 1,9-dibromononane under the same reaction conditions as described for the alkylation of compound of formula VI with VII.

Ester intermediates of formula VI can be easily prepared by conventional ester synthesis starting from acid IV and alcohol II followed by deprotection of the obtained compound of formula V (see for reference Green's Protective Groups in Organic Synthesis Fourth Edition, Wiley-Interscience Publication, which is incorporated herein by reference in it is entirety). The ester formation reaction can be performed under several different conditions in the presence of acid activating agent such as dicyclohexylcarbodiimide (DCC), 1-ethyl-3-[3-dimethylaminopropyl]carbodiimide hydrochloride (EDC), 2-(1H-benzotriazol-1-yl)-1,1,3,3,-tetramethyluronium hexafluorophosphate (HBTU) or converting first the acid into the corresponding acyl chloride with $SOCl_2$ or oxalyl chloride. Alternatively, the hydroxyl group of alcohol II can be converted into a LG, as described above for the preparation of intermediate XI from VIII, and then reacted with the acid VI in a polar aprotic solvent (e.g. acetonitrile or DMF) in the presence of a base such as for example, sodium, potassium or cesium carbonate.

An alternative route for the preparation of compounds of general formula (I) entails the alkylation of amino intermediate VI with XIV followed by removal of protecting groups previously introduced. This alkylation reaction can be accomplished under classical reaction conditions already described for the preparation of intermediate VIII from VI.

Preparation of compounds of formula XIV can be accomplished by reaction of intermediate XIII with a bifunctional reagent such as, for the this example, 1,9-dibromononane (as described above for the preparation of intermediate VIII from VI) and can be easily extended to the preparation of other analogues.

Intermediate of formula XIII can be prepared by treating the epoxide of general formula XII with benzyl amines. The reaction can be performed neat or in a high boiling point solvent such as toluene, dioxane, or butanol. The reaction proceeds smoothly by thermal or microwave heating and is completed over a period of time ranging from 1 to 24 hours at 80 to 120° C. Alternatively this intermediate can be prepared by alkylation of intermediate XVI under the already described conditions for the alkylation of amine with alkyl bromides.

The synthesis of intermediates of general formula XI and XVI, wherein Q is a group of formula Q1 and PG1 is a benzyl group protecting the phenolic hydroxyl moiety, is described in US 2004/224982, which is incorporated herein by reference in its entirety.

Intermediates of general formula XII, wherein Q is a group of formula Q1 and PG1 is a benzyl group protecting the phenolic hydroxyl moiety, can be easily prepared from intermediate XI, as described in WO 2008/104781, which is incorporated herein by reference in its entirety.

The preparation of intermediate IX, wherein Q is a group of formula Q1 and Z is OH, can be achieved from intermediate XVI by reaction with alkaline azide salt in a polar solvent such as DMF or DMSO at 80° C. or higher temperature followed by well known reduction of azide under catalytic hydrogenation conditions or by using another reducing agent such as $PPh_3$ and removal of the introduced protecting group.

The compounds of general formula IV are commercially available or, in the case $R_1$ and $R_2$ have the meanings cited above and $R_3$ is hydroxyl, they can be prepared by reaction of a suitable α-keto ester of formula XX with the appropriate Grignard reagent of formula XXI. The reaction is performed in an aprotic solvent such as THF at −20° C. or lower temperature and leads to an acid of general formula IV where $R_1$ and $R_2$ have the meaning cited above and $R_3$ is an hydroxyl group.

The invention also provides pharmaceutical compositions of compounds of formula (I) in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety Administration of the compounds of the present invention may be accomplished according to patient needs, for example, orally, nasally, parenterally (subcutaneously, intravenously, intramuscularly, intrasternally, and by infusion), by inhalation, rectally, vaginally, topically, locally, transdermally, and by ocular administration.

Various solid oral dosage forms can be used for administering compounds of the present invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants, and the like. Time release capsules, tablets and gels are also advantageous in administering the compounds of the present invention.

Various liquid oral dosage forms can also be used for administering compounds of the present invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates, and polyethylene glycols.

Formulations for vaginal administration can be in the form of cream, gel, paste, foam, or spray formula containing, in addition to the active ingredient, such suitable carriers as are also known.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case, the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the present invention.

Inhalation aerosols containing a propellant gas such as a hydrofluoroalkane may contain the compounds of the present invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic or hydroalcoholic medium, and they may be delivered by jet or ultrasonic nebulizers known from the prior art or by soft-mist nebulizers such as Respimat®.

The compounds of the present invention may be administered as the sole active agent or in combination with other pharmaceutical active ingredients including those currently used in the treatment of respiratory disorders, e.g. corticosteroids, P38 MAP kinase inhibitors, IKK2, HNE inhibitors, PDE4 inhibitors, leukotriene modulators, NSAIDs, and mucus regulators.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage of 0.001 to 1000 mg/day, preferably 0.1 to 500 mg/day.

When the compounds of formula (I) are administered by the inhalation route, they are preferably given at a dosage of 0.001 to 500 mg/day, preferably 0.1 to 200 mg/day.

The compounds of formula (I) may be administered for the prevention and/or treatment of broncho-obstructive or inflammatory diseases, such as asthma, chronic bronchitis, chronic obstructive pulmonary disease (COPD), bronchial hyperreactivity, cough, emphysema or rhinitis; urological disorders such as urinary incontinence, pollakiuria, cystospasm, chronic cystitis and overactive bladder (OAB); gastrointestinal disorders such as bowel syndrome, spastic colitis, diverticulitis, peptic ulceration, gastrointestinal motility or gastric acid secretion; dry mouth; mydriasis, tachycardia; ophthalmic interventions cardiovascular disorders such as vagally induced sinus bradycardia.

Other features of the invention will become apparent in the course of the following descriptions of exemplary embodiments which are given for illustration of the invention and are not intended to be limiting thereof.

EXAMPLES

The LCMS methods A and B, used for the characterization of the compounds of the present invention, are described in the following:

| Method A (IS 10 cm_ESCI_Formic_MeCN) | | |
|---|---|---|
| HPLC Setup | | |
| Solvents: | Acetonitrile (Far UV grade) with 0.1% (V/V) formic acid Water (High purity via PureLab Option unit) with 0.1% formic acid | |
| Column: | Phenomenex Luna 5μ C18 (2), 100 × 4.6 mm. (Plus guard cartridge) | |
| Flow Rate: | 2 ml/min | |
| Gradient: | A: Water/formic    B: MeCN/formic | |
| Time | A % | B % |
| 0.00 | 95 | 5 |
| 3.50 | 5 | 95 |
| 5.50 | 5 | 95 |
| 5.60 | 95 | 5 |
| 6.50 | 95 | 5 |

Ionization is either electrospray (ESI) or atmospheric-pressure chemical ionization (APCI).
UV detection via HP or Waters DAD Start Range (nm) 210    End Range (nm) 400    Range interval (nm) 4.0
MS detection
Micromass ZQ, single quadrapole instrument.
Scan range for MS Data (m/z)
Start (m/z)  100
End (m/z)  650 or 1000 when required
With +ve/−ve switching

| Method B (IS 15 cm_Formic_ASCENTIS_HPLC_CH$_3$CN) | | |
|---|---|---|
| HPLC Setup | | |
| Solvents: | Acetonitrile (Far UV grade) with 0.1% (V/V) formic acid Water (High purity via PureLab Ultra unit) with 0.1% formic acid | |
| Column: | Supelco, Ascentis ® Express C18 or Hichrom Halo C18, 2.7 μm C18, 150 × 4.6 mm. | |
| Flow Rate: | 1 ml/min | |
| Gradient: | A: Water/formic    B: MeCN/formic | |
| Time | A % | B % |
| 0.00 | 96 | 4 |
| 3.00 | 96 | 4 |
| 9.00 | 0 | 100 |
| 13.6 | 0 | 100 |
| 13.7 | 96 | 4 |
| 15 | 96 | 4 |

Instrument: Agilent 1100, Binary Pump, Agilent Sampler and Agilent DAD detector
Diode array detection: (300 nm, Band Width 200 nm; Ref 450 nm, Band Width 100 nm).

The intermediate compounds for the synthesis of final compounds of general formula (I) were obtained through the preparations herebelow described.

Preparation intermediate 1. 9-Bromononanoic acid

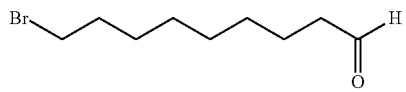 [SMILES: O=CCCCCCCCCBr]

Pyridinium chlorochromate (38.7 g, 180 mmol) and silica 60A (39 g, particle size 35-70 micron) suspended in dichloromethane (250 mL) were stirred at RT for 45 minutes. 9-Bromononanol (26.7 g, 120 mmol) was added, in one portion, and the suspension was stirred at RT for 18 hours. The reaction mixture was filtered through a column of celite and the resultant filtrate concentrated under vacuum affording the title compound (28.0 g, >100%).
The material was used without further purification in the next step.
¹H NMR (400 MHz, CHCl₃-d): δ 9.77 (s, 1H), 3.41 (t, 2H), 2.43 (t, 2H), 1.90-1.80 (m, 2H), 1.63 (s, 2H), 1.43 (s, 2H), 1.32 (s, 6H).

Preparation intermediate 2.
2-(8-Bromooctyl)-1,3-dioxolane

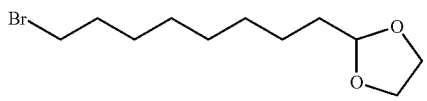 [SMILES: BrCCCCCCCCC1OCCO1]

9-Bromononanal (28.0 g, assumed 120 mmol), ethylene glycol (33.6 mL, 600 mmol) and para-toluenesulphonic acid (2.7 g, 13 mmol) in toluene (210 mL) were heated at reflux for 20 hours. The reaction was cooled to RT and quenched with saturated aqueous sodium bicarbonate solution (300 mL). The resultant mixture was extracted with diethyl ether (×2). The combined organic extracts were washed with saturated aqueous sodium bicarbonate solution, water and brine (100 mL). The organic phase was dried (magnesium sulphate), filtered and evaporated under reduced pressure to afford the title compound (25.2 g, 79%).
¹H NMR (400 MHz, CHCl₃-d): δ 4.84 (t, 1H), 3.95-3.78 (m, 4H), 3.43-3.37 (m, 2H), 1.90-1.79 (m, 2H), 1.69-1.54 (m, 2H), 1.42 (s, 3H), 1.32 (s, 7H).
All other 1,3-dioxalanes (i.e. 2-(7-bromoheptyl)-1,3-dioxolane; 2-(6-bromohexyl)-1,3-dioxolane; 2-(5-bromopentyl)-1,3-dioxolane and 2-(4-bromobutyl)-1,3-dioxolane) were prepared by the same method.

Preparation intermediate 3. 8-(Benzyloxy)-5-(2-bromoacetyl)quinolin-2(1H)-one

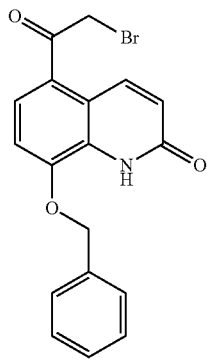 [SMILES: O=C(CBr)c1ccc(OCc2ccccc2)c2[nH]c(=O)ccc12]

To a suspension of 5-acetyl-8-(benzyloxy)quinolin-2(1H)-one (19.4 g, 66.4 mmol) in anhydrous THF (240 mL) and anhydrous methanol (165 mL), a solution of tetra-n-butylammonium tribromide (54.5 g, 113.0 mmol) in anhydrous THF (130 mL) was added dropwise over 1.5 hours. The resultant solution was stirred at RT overnight before concentrating under reduced pressure without heating. The residue was re-dissolved in methanol (200 mL). Saturated aqueous ammonium chloride solution (390 mL) was added with ice-cooling. The resultant suspension was filtered, and the solid was washed with water and dried under vacuum. The solid was suspended in dichloromethane and methanol (1:1 v/v, 100 mL) for 90 minutes. The solid was collected by filtration, washed with dichloromethane and air-dried to afford the title compound (18.0 g, 73%).
¹H NMR (400 MHz, CDCl₃-d): δ 9.23 (br s, 1H), 8.78 (d, 1H), 7.67 (d, 1H), 7.40 (s, 5H), 7.03 (d, 1H), 6.75 (d, 1H), 5.25 (s, 2H), 4.42 (s, 2H).

Preparation intermediate 4. (R)-8-(Benzyloxy)-5-(2-bromo-1-hydroxyethyl)quinolin-2(1H)-one

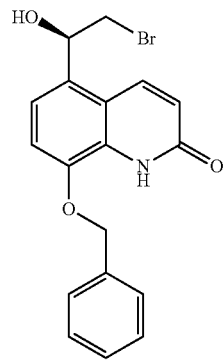 [SMILES: O=c1ccc2c([C@@H](O)CBr)ccc(OCc3ccccc3)c2[nH]1]

8-(Benzyloxy)-5-(2-bromoacetyl)quinolin-2(1H)-one (26.0 g, 69.9 mmol) and (R)-3,3-diphenyl-1-methyltetrahydro-3H-pyrrolo[1,2-c][1,3,2]oxazaborole (21.3 g, 76.8 mmol) were azeotroped with toluene (×3) then suspended in anhydrous THF (400 mL) under an atmosphere of nitrogen. The suspension was cooled to −20° C. (external temperature), and borane dimethyl sulfide complex solution (45.4 mL, 90.8 mmol, 2.0 M solution in THF) was added by syringe pump over 3 hours. After complete addition the reaction mixture was stirred for an hour before quenching with methanol (25 mL). The reaction was warmed to RT over 20 minutes. The mixture was concentrated in vacuo and the residue was suspended in aqueous hydrochloric acid (500 mL, 1 M solution) and stirred at RT for 18 hours. After this time, the solid was collected by filtration and washed with water (×3). The solid was partially dissolved in ethyl acetate and heated at reflux for 2 hours. The remaining solid was removed by hot filtration, and the filtrate was evaporated to afford the title compound. The solid collected from the hot ethyl acetate was again partially dissolved in ethyl acetate and heated at reflux for 2 hours then filtered to give filtrate containing pure product. This process was repeated four more times. The combined solid was recrystallised from ethyl acetate and petroleum ether to afford the title compound (20.0 g, 76%).
¹H NMR (400 MHz, DMSO): δ 10.68 (s, 1H), 8.19 (d, J=9.9 Hz, 1H), 7.58 (d, J=7.5 Hz, 2H), 7.41-7.36 (m, 2H), 7.34-7.29 (m, 1H), 7.23-7.19 (m, 2H), 6.57 (d, J=9.8 Hz, 1H), 5.94 (d, J=4.7 Hz, 1H), 5.31 (s, 2H), 5.25-5.19 (m, 1H), 3.71-3.58 (m, 2H).

Preparation intermediate 5. (R)-8-(Benzyloxy)-5-(2-bromo-1-(tert-butyldimethylsilyloxy)ethyl)-quinolin-2(1H)-one

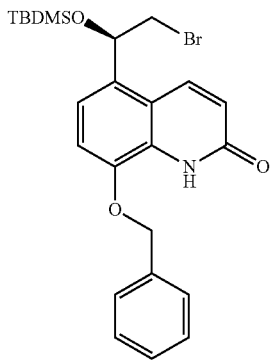 [SMILES: CC(C)(C)[Si](C)(C)O[C@@H](CBr)c1ccc(OCc2ccccc2)c2[nH]c(=O)ccc12]

2,6-Lutidine (6.9 mL, 59.5 mmol) was added to a solution of (R)-8-(benzyloxy)-5-(2-bromo-1-hydroxyethyl)quinolin-2(1H)-one (10.1 g, 27.0 mmol) in dichloromethane (100 mL) at 0° C. The reaction mixture was stirred for 5 minutes then tert-butyldimethylsilyl trifluoromethanesulfonate (13.0 mL, 56.8 mmol) was added dropwise over 15 minutes. The mixture was stirred at 0° C. for 30 minutes, followed by RT overnight. After this time, the reaction was quenched with saturated aqueous sodium bicarbonate solution and extracted with dichloromethane (×3). The combined organic extracts were dried (magnesium sulfate), filtered, and concentrated under reduced pressure. iso-Hexane (500 mL) was added to the crude material, and the resultant solid collected by filtration. The solid was recrystallised from ethyl acetate and petroleum ether (40:60) to afford the title compound (11.3 g, 85%).

$^1$H NMR (400 MHz, CDCl$_3$-d): δ 9.19 (s, 1H), 8.23 (dd, J=9.9, 4.4 Hz, 1H), 7.43 (d, J=4.6 Hz, 5H), 7.17 (dd, J=8.3, 4.5 Hz, 1H), 7.03 (dd, J=8.2, 4.4 Hz, 1H), 6.71 (dd, J=9.9, 3.7 Hz, 1H), 5.18 (d, J=4.5 Hz, 3H), 3.63-3.56 (m, 1H), 3.49 (dd, J=10.4, 4.8 Hz, 1H), 0.88 (t, J=4.4 Hz, 9H), 0.14 (d, J=4.4 Hz, 3H), −0.11 (d, J=4.4 Hz, 3H).

Preparation intermediate 6. (R)-5-(2-Azido-1-(tert-butyldimethylsilyloxy)ethyl)-8-(benzyloxy)-quinolin-2(1H)-one

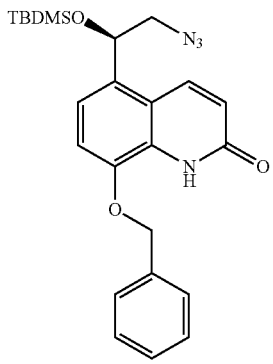 [SMILES: CC(C)(C)[Si](C)(C)O[C@@H](CN=[N+]=[N-])c1ccc(OCc2ccccc2)c2[nH]c(=O)ccc12]

(R)-8-(Benzyloxy)-5-(2-bromo-1-(tert-butyldimethylsilyloxy)ethyl)-quinolin-2(1H)-one (5.0 g, 10.2 mmol) was dissolved in dimethyl formamide (90 mL) and water (10 mL). Sodium iodide (1.7 g, 11.3 mmol) and sodium azide (0.7 g, 11.3 mmol) were added sequentially. The reaction mixture was stirred at RT until all the solid was in solution. The solution was heated at 80° C. for 40 hours then cooled to RT and diluted with water (300 mL). The aqueous layer was extracted with dichloromethane, and the combined organic extracts were dried (magnesium sulfate), filtered and concentrated under reduced pressure. The crude residue was recrystallised from ethyl acetate and iso-hexane to afford the desired compound, (3.6 g, 78%), used without further purification in the next step.

$^1$H NMR (400 MHz, CDCl$_3$-d): δ 9.19 (s, 1H), 8.18 (d, J=9.9 Hz, 1H), 7.45-7.36 (m, 4H), 7.20 (d, J=8.3 Hz, 1H), 7.04 (d, J=8.3 Hz, 1H), 6.70 (dd, J=9.9, 2.2 Hz, 1H), 5.19-5.13 (m, 3H), 3.48 (dd, J=12.7, 8.1 Hz, 1H), 3.26 (dd, J=12.7, 3.8 Hz, 1H), 0.89 (s, 9H), 0.14 (s, 3H), −0.11 (s, 3H).

Preparation intermediate 7. (R)-5-(2-Amino-1-(tert-butyldimethylsilyloxy)ethyl)-8-hydroxyquinolin-2(1H)-one formate

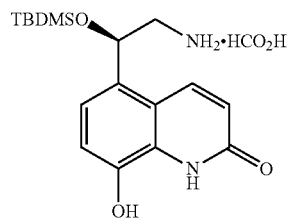

Palladium on activated carbon (0.4 g, 10% w/w) was added to a suspension of (R)-5-(2-azido-1-(tert-butyldimethylsilyloxy)ethyl)-8-(benzyloxy)quinolin-2(1H)-one (2.05 g, 4.60 mmol) and ammonium formate (2.87 g, 63 mmol) in methanol (50 mL). The reaction mixture was heated at 80° C. for 1 hour and then filtered through celite, washing with water. The reaction mixture was concentrated under reduced pressure. The resultant solid was washed with water, triturated with ethyl acetate and collected by filtration to afford the title compound (1.32 g, 86%).

$^1$H NMR (400 MHz, DMSO): δ 8.34 (s, 1H), 8.31-8.22 (m, 1H), 7.03 (d, J=8.1 Hz, 1H), 6.98-6.90 (m, 1H), 6.53 (d, J=9.9 Hz, 1H), 5.13 (t, J=6.0 Hz, 1H), 3.18 (s, 1H), 2.84-2.73 (m, 2H), 0.83 (s, 9H), 0.06 (s, 3H), −0.17 (s, 3H).

(R)-5-(2-Amino-1-(tert-butyldimethylsilyloxy)ethyl)-8-hydroxyquinolin-2(1H)-one.

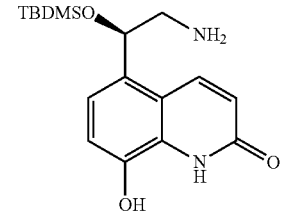 [SMILES: CC(C)(C)[Si](C)(C)O[C@@H](CN)c1ccc(O)c2[nH]c(=O)ccc12]

To an ice-cooled suspension of palladium on activated carbon (4.50 g, 10% w/w) and (R)-5-(2-azido-1-(tert-butyldimethylsilyloxy)ethyl)-8-(benzyloxy)quinolin-2(1H)-one (4.50 g, 10.0 mmol) in ethanol (50 mL) was added dropwise 1-methyl-1,4-cyclohexadiene (11.0 mL, 97.9 mmol). The coolant was removed, and the suspension stirred at ambient temperature for 10 minutes and then heated to 50° C. for one hour. The reaction mixture was allowed to cool and the suspension filtered through celite. The filter-cake was washed with further ethanol, and the combined filtrates concentrated under reduced pressure. The residue was triturated with acetonitrile to afford the title compound (3.03 g, 90%).

Preparation intermediate 8. (R)-5-(2-Amino-1-hydroxyethyl)-8-hydroxyquinolin-2(1H)-one hydrochloride

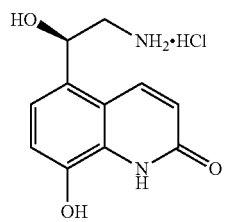

(R)-5-(2-Amino-1-(tert-butyldimethylsilyloxy)ethyl)-8-hydroxyquinolin-2(1H)-one formate (0.23 g, 0.61 mmol) was dissolved in hydrochloric acid (5 mL, 4 M solution in dioxane) and methanol (5 mL). The reaction mixture was stirred at RT for 16 hours before concentrating in vacuo. The resultant residue was washed with ethyl acetate and dried in a vacuum oven for 18 hours to afford the title compound (0.15 g, 99%).

$^1$H NMR (400 MHz, CD$_3$OD): δ 7.71 (d, J=9.8 Hz, 1H), 6.57 (d, J=8.2 Hz, 1H), 6.31 (d, J=8.2 Hz, 1H), 6.02 (dd, J=9.8, 6.5 Hz, 1H), 4.58 (dd, J=9.6, 3.5 Hz, 1H), 2.47-2.31 (m, 2H).

Preparation intermediate 9. Ethyl 2-hydroxy-2-phenyl-2-(thiophen-3-yl)acetate

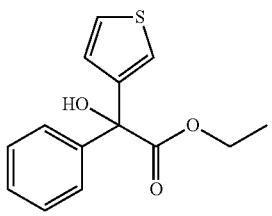 [SMILES: CCOC(=O)C(O)(c1ccccc1)c1ccsc1]

To a stirred solution of ethyl benzoyl formate (1.30 g, 7.30 mmol) in THF (5 mL) at −78° C. under nitrogen atmosphere, 3-thienylmagnesium iodide (29.2 mL, 8.76 mmol) was added over 10 minutes. After stirring at −78° C. for 1 hour, the reaction mixture was allowed to warm to RT and stirred overnight. The reaction mixture was quenched with saturated aqueous ammonium chloride solution and extracted with ethyl acetate (×3). The combined organic extracts were washed with brine, dried (magnesium sulfate), filtered, and concentrated under reduced pressure. The crude material was purified by silica gel column chromatography eluting with 0-10% ethyl acetate in iso-hexane to afford the title compound (1.06 g, 55%).

$^1$H NMR (400 MHz, CDCl$_3$-d): δ 7.45-7.39 (m, 2H), 7.37-7.28 (m, 5H), 7.12-7.09 (m, 1H), 4.38-4.28 (m, 2H), 4.30-4.25 (m, 1H), 1.32-1.24 (m, 3H).

Preparation intermediate 10. 2-Hydroxy-2-phenyl-2-(thiophen-3-yl)acetic acid

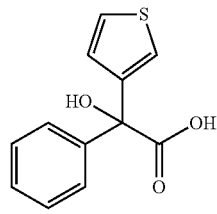 [SMILES: O=C(O)C(O)(c1ccccc1)c1ccsc1]

To a stirred solution of ethyl 2-hydroxy-2-phenyl-2-(thiophen-3-yl)acetate (1.06 g, 4.02 mmol) in THF (10 mL), sodium hydroxide (10 mL, 2.0 M aqueous solution) was added. The reaction was heated at 60° C. for 24 hours. The reaction was allowed to cool to RT, and THF was removed under reduced pressure. The resultant residue was washed with diethyl ether (×3). The aqueous layer was acidified to pH 1 with 2.0 M aqueous hydrochloric acid and extracted with ethyl acetate (×3). The combined ethyl acetate layers were washed with saturated sodium chloride solution, dried (magnesium sulfate), filtered and concentrated in vacuo to afford the title compound (0.75 g, 79%).

$^1$H NMR (400 MHz, CDCl$_3$-d): δ 13.20 (br s, 1H), 7.52 (d, J=2 Hz, 1H), 7.49-7.28 (m, 6H), 7.05 (d, J=2 Hz, 1H), 6.56 (br s, 1H)

The final compounds were prepared as described below with the use of the appropriate acid (1) and the appropriate bromo-1,3-dioxalanes.

Preparation intermediate 11. tert-Butyl 4-(tosyloxymethyl)piperidine-1-carboxylate

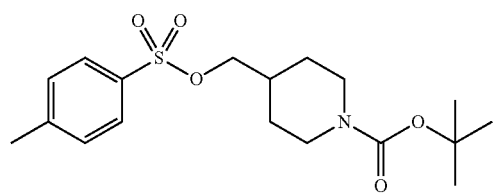 [SMILES: Cc1ccc(S(=O)(=O)OCC2CCN(C(=O)OC(C)(C)C)CC2)cc1]

To a stirred solution of tert-butyl 4-(hydroxymethyl)piperidine-1-carboxylate (5.0 g, 23.2 mmol) in anhydrous pyridine (18.5 mL) at 0° C. under nitrogen, p-toluenesulfonyl chloride (4.87 g, 25.55 mmol) was added in one portion. The reaction was stirred at 0° C. for 100 minutes before warming to RT. After 18 hours, the reaction mixture was poured into water (100 mL) and extracted with ethyl acetate (3×50 mL). The combined organic extracts were washed with aqueous hydrochloric acid (2×100 mL, 1.0 M solution), saturated sodium chloride solution, dried (magnesium sulfate), filtered, and concentrated in vacuo to yield the title compound (7.87 g, 91%).

$^1$H NMR (400 MHz, CDCl$_3$-d): δ 7.77-7.70 (m, 2H), 7.31 (d, J=8.0 Hz, 2H), 3.80 (d, J=6.5 Hz, 2H), 2.61 (d, J=13.1 Hz, 2H), 2.41 (s, 3H), 1.84-1.72 (m, 1H), 1.60 (d, J=13.1 Hz, 2H), 1.46-1.36 (m, 9H), 1.05 (ddd, J=24.9, 12.5, 4.4 Hz, 2H), −0.05 (t, J=3.3 Hz, 2H).

Preparation intermediate 12. tert-Butyl 4-((2-cyclo-hexyl-2-hydroxy-2-phenylacetyloxy)methyl)-piperi-dine-1-carboxylate

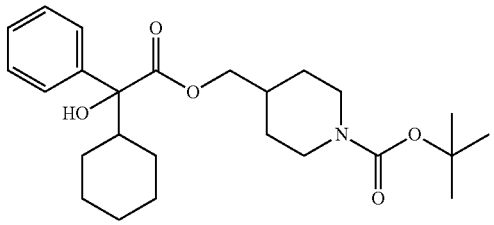 [SMILES: CC(C)(C)OC(=O)N1CCC(COC(=O)C(O)(c2ccccc2)C2CCCCC2)CC1]

Cyclohexylmandelic acid (885 mg, 3.78 mmol) was added to tert-butyl 4-(bromomethyl)piperidine-1-carboxylate (957 mg, 3.44 mmol) and potassium carbonate (713 mg) in dimethyl formamide (10 mL) at RT with stirring. After 72 hours, the reaction was diluted with ethyl acetate and water. The organic extracts were washed with saturated sodium chloride solution, dried (sodium sulfate), filtered, and concentrated under reduced pressure. The crude reaction mixture was purified by silica gel column chromatography eluting with 0-30% ethyl acetate in iso-hexane to afford the title compound (1.10 g, 75%).

$^1$H NMR (400 MHz, CDCl$_3$-d): δ 7.64-7.59 (m, 2H), 7.37-7.30 (m, 2H), 7.31-7.25 (m, 1H), 4.15-4.04 (m, 2H), 4.05-3.97 (m, 2H), 3.68 (s, 1H), 2.73-2.60 (m, 2H), 2.28-2.17 (m, 1H), 1.83-1.76 (m, 2H), 1.70-1.53 (m, 4H), 1.46 (s, 9H), 1.42 (dd, J=8.3, 3.4 Hz, 2H), 1.32-1.03 (m, 7H).

Preparation intermediate 13. Piperidin-4-ylmethyl 2-cyclohexyl-2-hydroxy-2-phenylacetate hydrochloride

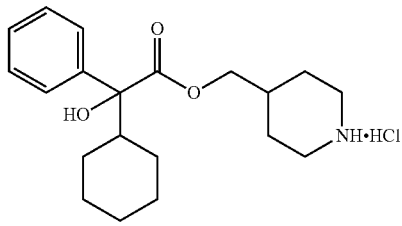

tert-Butyl 4-((2-cyclohexyl-2-hydroxy-2-phenylacetyloxy)methyl)-piperidine-1-carboxylate (1.10 g, 2.55 mmol) was dissolved in hydrochloric acid (5 mL, 4 M solution in dioxane) and dichloromethane (5 mL). The reaction mixture was stirred at RT for 3 hours and concentrated under reduced pressure to afford the title compound (970 mg, >100%) that was used without further purification in the next step.

$^1$H NMR (400 MHz, CDCl$_3$-d): δ 9.79-9.64 (bs, 1H), 9.58-9.40 (bs, 1H), 7.63-7.59 (m, 2H), 7.37-7.30 (m, 2H), 7.29-7.25 (m, 1H), 4.10 (dd, J=11.0, 6.3 Hz, 1H), 4.03-3.97 (m, 1H), 3.65 (s, 1H), 3.47 (d, J=13.0 Hz, 2H), 2.79 (s, 2H), 2.29-2.22 (m, 1H), 1.92-1.61 (m, 8H), 1.51-1.23 (m, 4H), 1.21-1.05 (m, 3H).

Preparation intermediate 14. (1-(9-(1,3-Dioxolan-2-yl)nonyl)piperidin-4-yl)methyl 2-cyclohexyl-2-hydroxy-2-phenylacetate

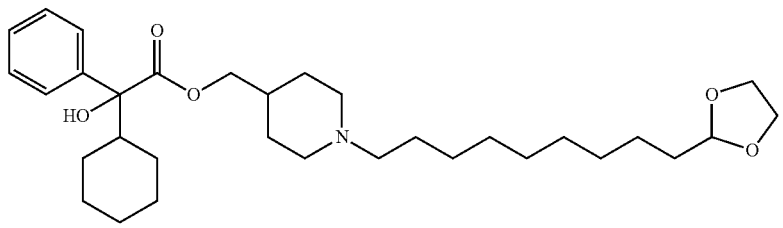 [SMILES: O=C(OCC1CCN(CCCCCCCCCC2OCCO2)CC1)C(O)(c1ccccc1)C1CCCCC1]

2-(8-Bromooctyl)-1,3-dioxolane (218 mg, 0.82 mmol) followed by di-isopropylethylamine (361 μL, 2.07 mmol) were added to a solution of piperidin-4-ylmethyl 2-cyclohexyl-2-hydroxy-2-phenylacetate hydrochloride (252 mg, 0.69 mmol) in acetonitrile (4 mL). The reaction mixture was heated at 60° C. for 17 hours. After this time, the reaction was cooled to RT and diluted with dichloromethane. The organic extracts were washed with water, filtered through a hydrophobic frit, and concentrated under reduced pressure. The crude material was purified by silica gel column chromatography eluting with 100% dichloromethane to 40:1 dichloromethane:methanol to afford the title compound that was used without further purification in the next step.

$^1$H NMR (400 MHz, CDCl$_3$-d): δ 7.63 (d, J=7.8 Hz, 2H), 7.33 (t, J=7.7 Hz, 2H), 4.84 (t, J=4.8 Hz, 1H), 4.03-3.93 (m, 3H), 3.87-3.82 (m, 2H), 3.69 (s, 1H), 2.94 (s, 2H), 2.37-2.20 (m, 3H), 1.96-1.72 (m, 3H), 1.70-1.06 (m, 32H).

Preparation intermediate 15. (1-(10-Oxodecyl)piperidin-4-yl)methyl 2-cyclohexyl-2-hydroxy-2-phenylacetate

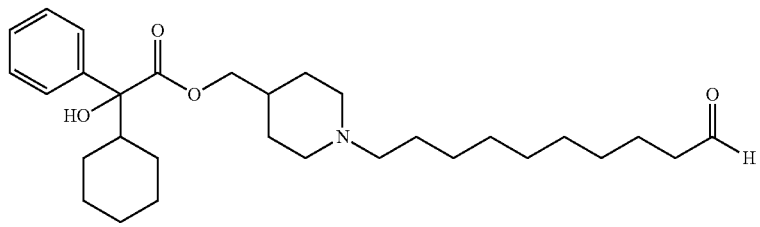 [SMILES: O=CCCCCCCCCCN1CCC(COC(=O)C(O)(c2ccccc2)C2CCCCC2)CC1]

(1-(9-(1,3-Dioxolan-2-yl)nonyl)piperidin-4-yl)methyl 2-cyclohexyl-2-hydroxy-2-phenylacetate (200 mg, 0.39 mmol) was dissolved in THF (2 mL) and hydrochloric acid (4 mL, 2 M aqueous solution) with stirring at RT. After 3 hours, the reaction mixture was diluted with ethyl acetate and washed with 10% aqueous potassium carbonate solution. The layers were separated and the organic extracts run through a hydrophobic frit. The solvents were removed in vacuo. The title compound was isolated (190 mg, >100%) and it was used without further purification in the next step.

Preparation intermediate 16. tert-Butyl 4-((2-hydroxy-2-phenyl-2-(thiophen-3-yl)acetyloxy)-methyl)piperidine-1-carboxylate

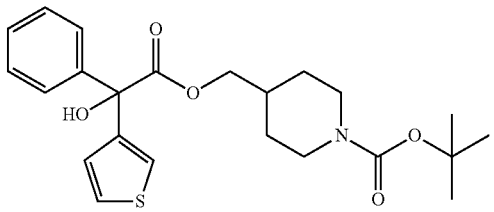 [SMILES: CC(C)(C)OC(=O)N1CCC(COC(=O)C(O)(c2ccccc2)c2ccsc2)CC1]

To a stirred solution of 2-hydroxy-2-phenyl-2-(thiophen-3-yl)acetic acid (0.75 g, 3.197 mmol) in toluene (4 mL) and dimethyl formamide (0.4 mL), 1,8-diazabicyclo[5.4.0]undec-7-ene (735 µL, 4.919 mmol) was added followed by tert-butyl 4-(tosyloxymethyl)piperidine-1-carboxylate (0.909 g, 2.459 mmol) in toluene (3.5 ml) and dimethyl formamide (0.35 mL). The reaction mixture was heated at 100° C. overnight. After this time, the reaction mixture was cooled to RT and concentrated in vacuo. The crude mixture purified by silica gel column chromatography eluting with a gradient of iso-hexane:ethyl acetate (1:0 to 3:1) to afford the title compound (0.84 g, 79%).

$^1$H NMR (400 MHz, CDCl$_3$-d): δ 7.44-7.38 (m, 2H), 7.37-7.28 (m, 5H), 7.08 (dd, J=5.0, 1.4 Hz, 1H), 4.24 (s, 1H), 4.13-4.05 (m, 2H), 2.76-2.44 (m, 3H), 1.82-1.69 (m, 1H), 1.64-1.26 (m, 12H); 1.11-0.98 (m, 2H).

Preparation intermediate 17. Piperidin-4-ylmethyl 2-cyclohexyl-2-hydroxy-2-phenylacetate tosylate

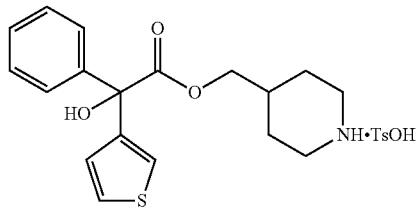

To a stirred solution of tert-butyl 4-((2-hydroxy-2-phenyl-2-(thiophen-3-yl)acetyloxy)methyl)piperidine-1-carboxylate (0.84 g, 1.94 mmol) in acetonitrile (10 mL), p-toluenesulfonic acid monohydrate (0.55 g, 2.91 mmol) was added. The reaction was stirred at 30° C. overnight and then concentrated under reduced pressure to afford the title compound (1.17 g, >100%) that was used without further purification in the next step.

Preparation intermediate 18. tert-Butyl 4-((3-hydroxy-2,2-diphenylpropanoyloxy)-methyl)-piperidine-1-carboxylate used for the preparation of Example 20

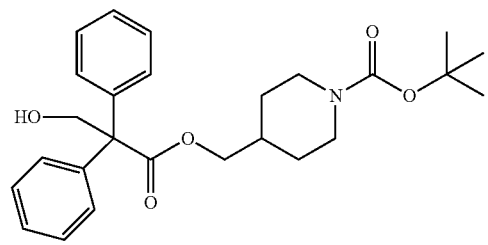 [SMILES: CC(C)(C)OC(=O)N1CCC(COC(=O)C(CO)(c2ccccc2)c2ccccc2)CC1]

tert-Butyl 4-((2,2-diphenylacetyloxy)methyl)piperidine-1-carboxylate (prepared as in Preparation intermediate 12 with 2,2-diphenylacetic acid replacing cyclohexylmandelic acid) (0.40 g, 0.98 mmol) in THF (5 mL) was treated with lithium hexamethyldisilazide (1.17 mL, 1.17 mmol, 1.0 M solution in THF) followed by formaldehyde (0.20 g, 50% w/w). The reaction mixture was stirred at RT for 16 hours then quenched with saturated aqueous ammonium chloride solution. The aqueous layer was extracted with dichloromethane. The combined organic extracts were dried (magnesium sulfate), filtered, and concentrated under reduced pressure. The crude product was purified by silica gel column chromatography eluting with 30-60% ethyl acetate in petroleum ether (40:60) to afford the title compound (0.10 g, 23%).

$^1$H NMR (400 MHz, CDCl$_3$-d): δ 7.35-7.24 (m, 10H), 4.34 (d, J=7.2 Hz, 2H), 4.12-3.96 (m, 3H), 2.75-2.66 (m, 1H), 2.59 (s, 2H), 1.78-1.65 (m, 1H), 1.50-1.41 (m, 11H), 1.03 (ddd, J=24.9, 12.4, 4.4 Hz, 2H).

Preparation intermediate 19. tert-Butyl 4-((2-acetamido-2,2-diphenylacetyloxy)-methyl)piperidine-1-carboxylate used for the synthesis of Example 23

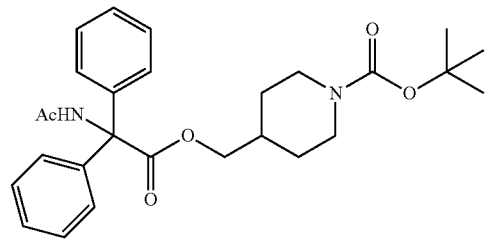 [SMILES: CC(=O)NC(C(=O)OCC1CCN(C(=O)OC(C)(C)C)CC1)(c1ccccc1)c1ccccc1]

To a solution of tert-butyl 4-((2-amino-2,2-diphenylacetyloxy)-methyl)piperidine-1-carboxylate (prepared as in Preparation intermediate 12 with diphenylglycine replacing cyclohexylmandelic acid) (0.50 g, 1.18 mmol) in DCM (1.5 mL) was added a solution of acetic anhydride (0.122 mL, 1.30 mmol) in DCM (0.5 mL). The reaction mixture was heated at 40° C. for 18 hours. The reaction mixture was allowed to cool to RT and further acetic anhydride (0.06 mL, 0.65 mmol) added. The reaction mixture was heated at 40° C. for a further 18 hours. The reaction mixture was allowed to cool to RT, quenched with water, and the mixture was stirred at RT for 1 hour. The reaction mixture was then partitioned between saturated aqueous sodium hydrogen carbonate and DCM. The organic phase was removed and the aqueous phase extracted with further DCM. The combined DCM extracts were washed with brine, dried (magnesium sulfate), filtered, and concentrated under reduced pressure. The product was isolated (0.541 g, >100%). The crude product was used without further purification in the next step.

Preparation intermediate 20. (1-(6-(4-Oxopiperidin-1-yl)hexyl)piperidin-4-yl)methyl 2-cyclohexyl-2-hydroxy-2-phenylacetate used for the synthesis of Example 28

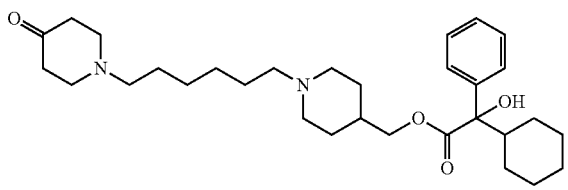 [SMILES: O=C1CCN(CCCCCCN2CCC(COC(=O)C(O)(c3ccccc3)C3CCCCC3)CC2)CC1]

To a stirred solution of (1-(6-oxohexyl)piperidin-4-yl)methyl 2-cyclohexyl-2-hydroxy-2-phenylacetate (prepared as Preparation intermediate 15 but using (1-(5-(1,3-dioxolan-2-yl)pentyl)piperidin-4-yl)methyl 2-cyclohexyl-2-hydroxy-2-phenylacetate (0.20 g, 0.47 mmol) and 1,4-dioxa-8-azaspiro[4.5]decane (0.133 g, 0.93 mmol) in THF (5 mL), sodium triacetoxyborohydride (0.294 g, 1.39 mmol) was added. The reaction mixture was stirred at RT for 18 hours. The reaction mixture was partitioned between DCM and saturated aqueous sodium hydrogen carbonate. The organic phase was removed, and the aqueous phase was extracted with further DCM. The combined organics were dried (magnesium sulfate), filtered, and concentrated under reduced pressure. The crude product was dissolved in THF (2 mL) and 2M aqueous HCl and heated at 60° C. for 18 hours. The reaction mixture was allowed to cool to RT and then quenched with saturated aqueous sodium hydrogen carbonate. The mixture was extracted twice with ethyl acetate. The organic phases were dried (magnesium sulfate), filtered and concentrated under reduced pressure. The product was isolated (0.193 g, 80%).

Example 1

(1-(9-((R)-2-Hydroxy-2-(8-hydroxy-2-oxo-1,2-dihydroquinolin-5-yl)ethylamino)nonyl)piperidin-4-yl) methyl 2-cyclohexyl-2-hydroxy-2-phenylacetate (compound 1)

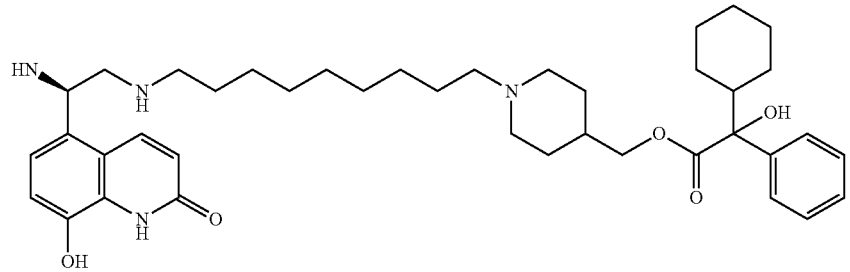 [SMILES: N[C@@H](CNCCCCCCCCCN1CCC(COC(=O)C(O)(c2ccccc2)C2CCCCC2)CC1)c1ccc(O)c2[nH]c(=O)ccc12]

Triethylamine (90 μL, 0.65 mmol) was added to a solution of (1-(10-oxodecyl)piperidin-4-yl)methyl 2-cyclohexyl-2-hydroxy-2-phenylacetate (182 mg, 0.39 mmol) and (R)-5-(2-amino-1-hydroxyethyl)-8-hydroxyquinolin-2(1H)-one hydrochloride (100 mg, 0.39 mmol) in methanol (4 mL). The reaction mixture was stirred at RT for 1 hour. Sodium triacetoxyborohydride (154 mg, 0.73 mmol) followed by acetic acid (74 μL, 1.29 mmol) were added, and the reaction mixture stirred at RT for 72 hours. The reaction was quenched with water (500 μL) and evaporated under reduced pressure. The residue was dissolved in dimethyl sulfoxide and submitted to reverse phase preparative HPLC for final purification. The title compound was isolated (42.3 mg, 16%).

$^1$H NMR (400 MHz, CD$_3$OD): δ 8.58 (s, 2H), 8.40 (d, J=9.8 Hz, 1H), 7.66-7.61 (m, 2H), 7.37-7.22 (m, 4H), 7.03 (d, J=8.1 Hz, 1H), 6.69 (d, J=9.8 Hz, 1H), 5.43-5.35 (m, 1H), 4.02 (d, J=6.2 Hz, 2H), 3.28-3.13 (m, 4H), 3.06-2.97 (m, 2H), 2.73-2.65 (m, 2H), 2.49-2.36 (m, 2H), 2.38-2.28 (m, 1H), 1.87-1.59 (m, 10H), 1.54-1.03 (m, 20H).

The following compounds of general formula (IA)

(IA)

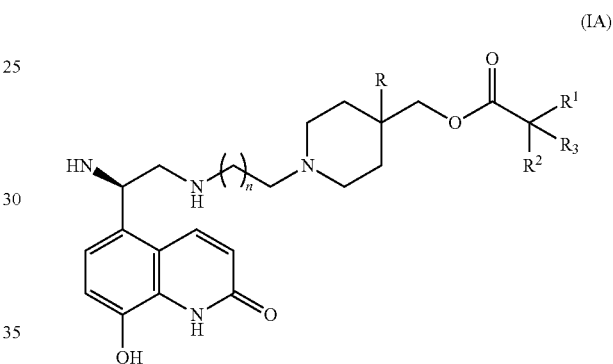

and compounds 28 to 31 (shown in the following table), were prepared using the procedure described for the preparation of compound 1 (in the $R_1$ meanings reported below, "c" stands for cyclic).

| Compound/Example | $R_1$ | $R_2$ | $R_3$ | R | n |
|---|---|---|---|---|---|
| 2 | c-C$_4$H$_7$ | phenyl | OH | H | 8 |
| 3 | c-C$_5$H$_9$ | phenyl | OH | H | 8 |
| 4 | phenyl | phenyl | OH | H | 8 |
| 5 | benzyl | phenyl | OH | H | 8 |
| 6 | c-C$_7$H$_{13}$ | phenyl | OH | H | 8 |
| 7 | c-C$_6$H$_{11}$ | phenyl | OH | Me | 8 |
| 8 | c-C$_6$H$_{11}$ | phenyl | H | H | 8 |
| 9 | c-C$_6$H$_{11}$ | 2-thienyl | OH | H | 8 |
| 10 | 3-thienyl | phenyl | OH | H | 8 |

-continued

| Compound/Example | R₁ | R₂ | R₃ | R | n |
|---|---|---|---|---|---|
| 11 | phenyl | phenyl | NH₂ | H | 8 |
| 12 | 2-thienyl | 2-thienyl | OH | H | 8 |
| 13 | phenyl | 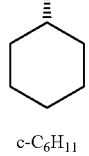 c-C₆H₁₁ | ◀━OH | H | 8 |
| 14 | phenyl | c-C₆H₁₁ | ⋯⋯OH | H | 8 |

-continued

| Compound/Example | R₁ | R₂ | R₃ | R | n |
|---|---|---|---|---|---|
| 15 | 2-thienyl | phenyl | OH | H | 8 |
| 16 | c-C₆H₁₁ | phenyl | OH | H | 7 |
| 17 | c-C₆H₁₁ | phenyl | OH | H | 6 |
| 18 | c-C₆H₁₁ | phenyl | OH | H | 4 |
| 19 | c-C₆H₁₁ | phenyl | OH | H | 5 |
| 20 | phenyl | phenyl | CH₂OH | H | 8 |
| 21 | c-C₆H₁₁ | c-C₆H₁₁ | OH | H | 8 |
| 22 | H | C(phenyl)₃ | H | H | 8 |
| 23 | phenyl | phenyl | NHAc | H | 8 |
| 24 | phenyl | 4-chlorophenyl | OH | H | 8 |
| 25 | c-C₆H₁₁ | 3-thienyl | OH | H | 8 |
| 26 | phenyl | 3-methoxyphenyl | OH | H | 8 |
| 27 | phenyl | 4-fluorophenyl | OH | H | 8 |

Example 28

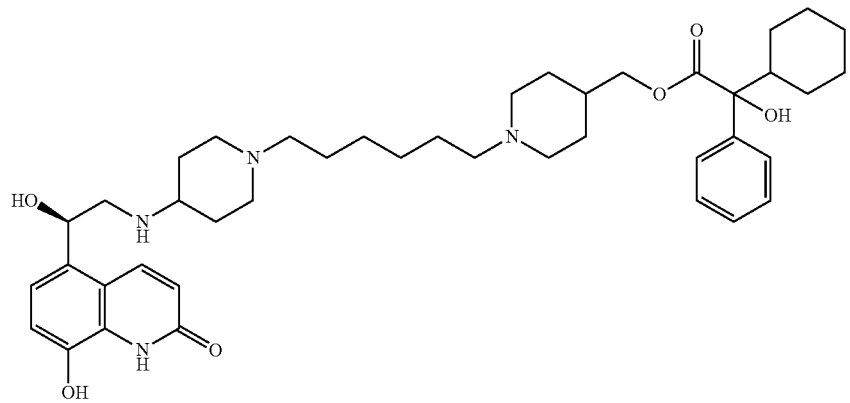 [SMILES: O=C(OCC1CCN(CCCCCCN2CCC(NC[C@H](O)c3ccc(O)c4[nH]c(=O)ccc34)CC2)CC1)C(O)(c1ccccc1)C1CCCCC1]

procedure described for the preparation of Compound 1, by replacing (1-(10-oxodecyl)piperidin-4-yl)methyl 2-cyclohexyl-2-hydroxy-2-phenylacetate with (1-(6-(4-oxopiperidin-1-yl)hexyl)piperidin-4-yl)methyl 2-cyclohexyl-2-hydroxy-2-phenylacetate whose synthesis is described in Preparation 20.

Example 29

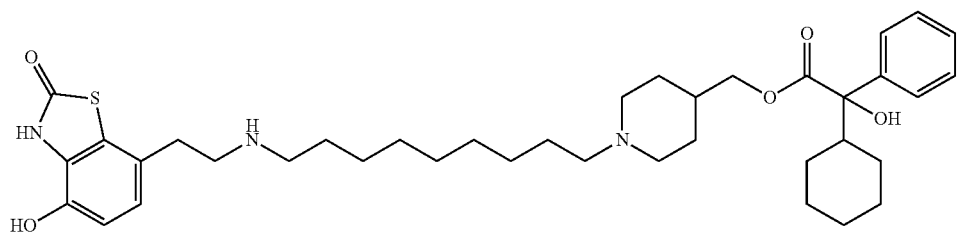 [SMILES: O=C(OCC1CCN(CCCCCCCCCNCCc2ccc(O)c3[nH]c(=O)sc23)CC1)C(O)(c1ccccc1)C1CCCCC1]

The compound of Example 29 was prepared using the methodology described for the preparation of compound 1, by replacing (R)-5-(2-amino-1-hydroxyethyl)-8-hydroxyquinolin-2(1H)-one hydrochloride with 7-(2-aminoethyl)-4-hydroxybenzo[d]thiazol-2(3H)-one hydrobromide (prepared as described in Organic Process Research & Development 2004, 8, 628-642, which is incorporated herein by reference in its entirety) in Example 1.

Example 30

(1-((E)-5-(3-(((R)-2-hydroxy-2-(8-hydroxy-2-oxo-1,2-dihydroquinolin-5-yl)ethyl)amino)propoxy)-4-methylpent-3-en-1-yl)piperidin-4-yl)methyl 2-cyclohexyl-2-hydroxy-2-phenylacetate

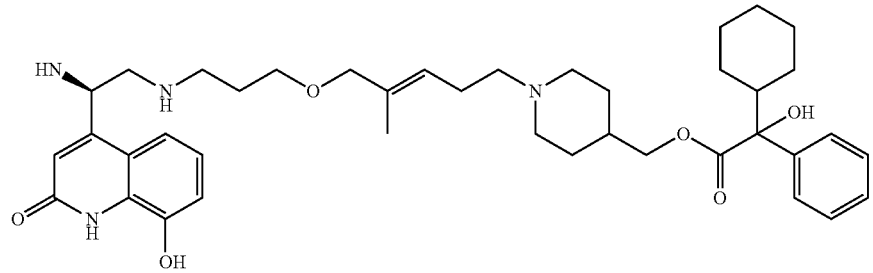 [SMILES: C/C(=C\CCN1CCC(COC(=O)C(O)(c2ccccc2)C2CCCCC2)CC1)COCCCNC[C@H](N)c1cc(=O)[nH]c2c(O)cccc12]

The preparation of Example 30 requires the synthesis of (E)-5-bromo-1-(3,3-diethoxypropoxy)-2-methylpent-2-ene to replace 2-(8-bromooctyl)-1,3-dioxolane.

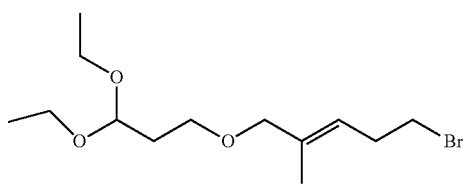 [SMILES: CCOC(CCOC/C(C)=C/CCBr)OCC]

Step 1.
3-(3,3-Diethoxypropoxy)-2-methylprop-1-ene

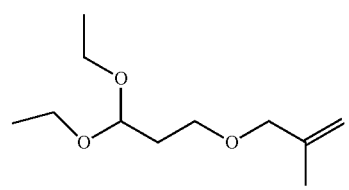

To a stirred solution of 3,3-diethoxy-1-propanol (3.0 g, 22.2 mmol) in anhydrous THF (50 mL) was added sodium hydride (60% dispersion in mineral oil, 1.07 g, 26.6 mmol). The reaction mixture was stirred for 30 minutes, and 3-bromo-2-methyl-1-propene (3.63 g, 24.5 mmol) then added. The reaction mixture was then stirred for a further 18 hours. The reaction mixture was quenched with saturated sodium hydrogen carbonate and extracted with ethyl acetate (×3). The combined organic extracts were washed with saturated aqueous sodium hydrogen carbonate solution and brine, dried (sodium sulfate), filtered and concentrated under reduced pressure to afford an oil (2.25 g, 50%). The material used in the next step without further purification.

Step 2. (E)-5-bromo-1-(3,3-diethoxypropoxy)-2-methylpent-2-ene

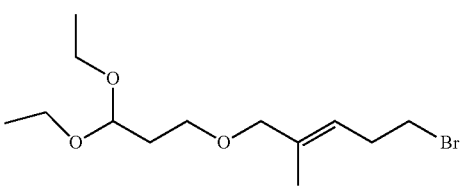 [SMILES: CCOC(CCOC/C(C)=C/CCBr)OCC]

To previously nitrogen degassed DCM (18 mL) was added Second Generation Grubbs Catalyst (0.225 g, 0.30 mmol) followed by 3-bromobutene (2.03 g, 15.0 mmol) and 3-(3,3-diethoxypropoxy)-2-methylprop-1-ene (1.52 g, 7.52 mmol). The reaction mixture was further degassed for 5 minutes and then heated under reflux for 2 hours. The solvent was concentrated under reduced pressure, and the residue was purified by silica gel column chromatography eluting with 0-100% ethyl acetate in iso-hexane to afford the title compound (0.208 g, 9%).

$^1$H NMR (400 MHz, CDCl$_3$): δ 5.47-5.32 (m, 1H); 4.69-4.62 (m, 1H); 3.85 (s, 2H); 3.72-3.61 (m, 2H); 3.58-3.32 (m, 6H); 2.63 (dd, J=14.3, 7.2 Hz, 2H); 1.94-1.85 (m, 2H); 1.66 (s, 3H); 1.28-1.15 (m, 6H).

Example 30

(R)-(1-(4-((6-((2-hydroxy-2-(8-hydroxy-2-oxo-1,2-dihydroquinolin-5-yl)ethyl)amino)hexyl)oxy)benzyl)piperidin-4-yl)methyl 2-hydroxy-2,2-diphenylacetate (compound 31)

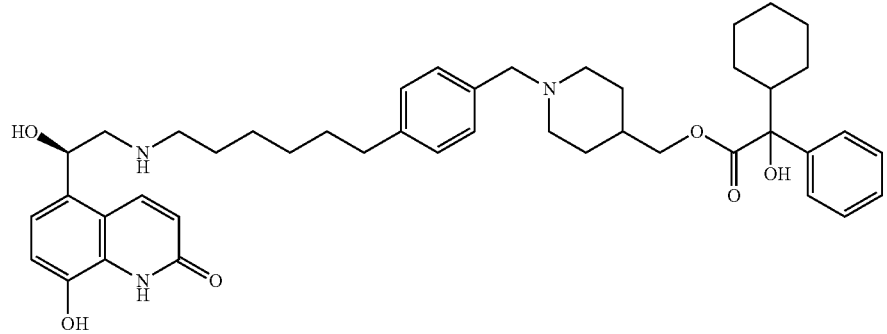 [SMILES: O=C(OCC1CCN(Cc2ccc(CCCCCCNC[C@H](O)c3ccc(O)c4[nH]c(=O)ccc34)cc2)CC1)C(O)(c1ccccc1)C1CCCCC1]

The preparation of compound 31 requires the synthesis of (1-(4-((5-(1,3-dioxolan-2-yl)pentyl)oxy)benzyl)piperidin-4-yl)methyl 2-hydroxy-2,2-diphenylacetate:

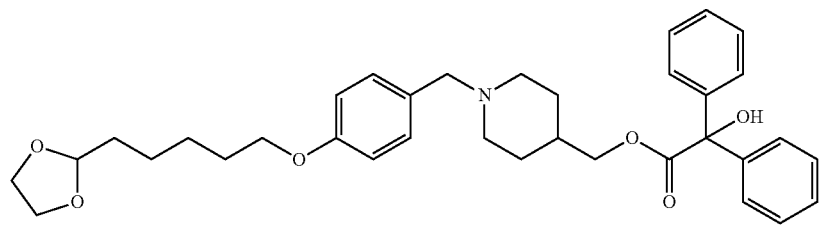 [SMILES: O=C(OCC1CCN(Cc2ccc(OCCCCCC3OCCO3)cc2)CC1)C(O)(c1ccccc1)c1ccccc1]

Step 1. 4-((5-(1,3-Dioxolan-2-yl)pentyl)oxy)benzaldehyde

To a stirred solution of 2-(5-bromopentyl)-1,3-dioxolane (4.38 g, 19.6 mmol) in dimethyl formamide (30 mL) was added 4-hydroxybenzaldehyde (3.00 g, 24.4 mmol) and potassium carbonate (4.52 g, 32.8 mmol). The reaction mixture was stirred at 50° C. for 16 hours. The reaction mixture was diluted with water and extracted with ethyl acetate (×3). The combined organic extracts were washed with saturated aqueous sodium hydrogen carbonate solution and brine, dried (sodium sulfate), filtered and concentrated under reduced pressure to afford an oil. The crude material was purified by silica gel column chromatography eluting with 0-100% ethyl acetate in iso-hexane to afford the title compound (1.92 g, 36%).

¹H NMR (400 MHz, CDCl₃): δ 9.92-9.86 (m, 1H); 7.85-7.80 (m, 2H); 7.03-6.95 (m, 2H); 4.87 (t, J=4.7 Hz, 1H); 4.07-3.80 (m, 6H); 1.89-1.79 (m, 2H); 1.75-1.67 (m, 2H), 1.58-1.46 (m, 4H).

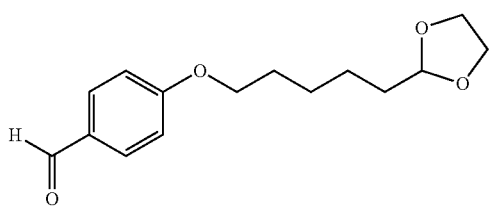 [SMILES: O=Cc1ccc(OCCCCCC2OCCO2)cc1]

Step 2. (1-(4-((5-(1,3-dioxolan-2-yl)pentyl)oxy)benzyl)piperidin-4-yl)methyl 2-hydroxy-2,2-diphenylacetate

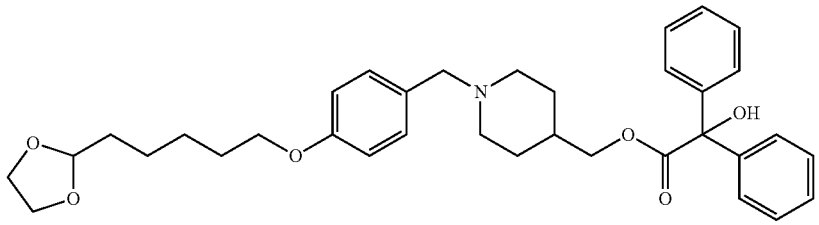 [SMILES: O=C(OCC1CCN(Cc2ccc(OCCCCCC3OCCO3)cc2)CC1)C(O)(c1ccccc1)c1ccccc1]

To a stirred solution of piperidin-4-ylmethyl 2-hydroxy-2,2-diphenylacetate (0.4 g, 1.23 mmol) and 4-((5-(1,3-dioxolan-2-yl)pentyl)oxy)benzaldehyde (0.38 g, 1.44 mmol) in DCM (5 mL) was added sodium triacetoxyborohydride (0.388 g, 1.83 mmol). The reaction mixture was stirred at room temperature for 18 hours. The reaction mixture was partitioned between EtOAc and saturated sodium hydrogen carbonate. The organic phase was dried (sodium sulfate), filtered, and concentrated under reduced pressure. The crude material was purified by silica gel column chromatography eluting with 1 to 10% methanol in ethyl acetate to afford the title compound as a colourless oil (0.50 g, 26%).

$^1$H NMR (400 MHz, CDCl$_3$): δ 7.43-7.37 (m, 5H); 7.35-7.29 (m, 5H); 7.23-7.08 (m, 2H); 6.92-6.78 (m, 2H); 4.86 (t, J=4.8 Hz, 1H); 4.25 (s, 1H); 4.13-3.79 (m, 10H); 3.44-3.30 (m, 2H); 2.80 (d, J=11.3 Hz, 2H); 1.92-1.65 (m, 7H); 1.57-1.42 (m, 4H); 1.28-1.11 (m, 2H).

Compounds 32 to 37 were prepared in the same fashion as compound 31 with the appropriate bromide (2-(5-bromopentyl)-1,3-dioxolane and 2-(4-bromobutyl)-1,3-dioxolane) used in Step 1 and the appropriate amine used in Step 2 (piperidin-4-ylmethyl 2-hydroxy-2,2-diphenylacetate or piperidin-4-ylmethyl 2-cyclohexyl-2-hydroxy-2-phenylacetate).

| Compound/Example | Structure |
|---|---|
| 32 | 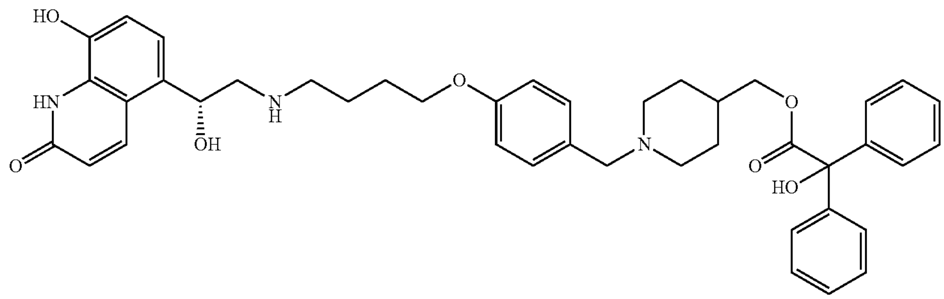 [SMILES: O=C(OCC1CCN(Cc2ccc(OCCCCNC[C@H](O)c3ccc(O)c4[nH]c(=O)ccc34)cc2)CC1)C(O)(c1ccccc1)c1ccccc1] |
| 33 | 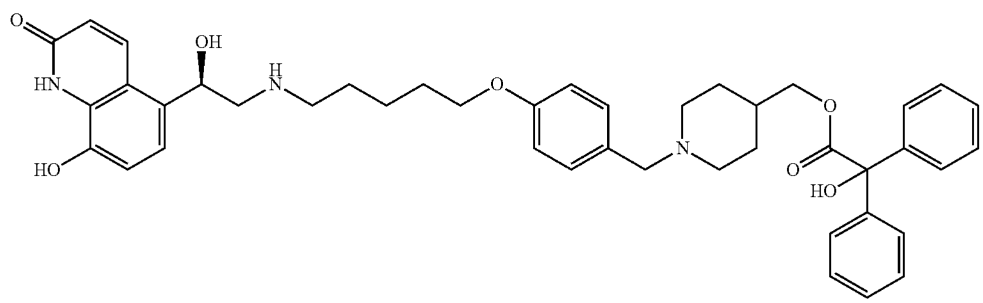 [SMILES: O=C(OCC1CCN(Cc2ccc(OCCCCCNC[C@H](O)c3ccc(O)c4[nH]c(=O)ccc34)cc2)CC1)C(O)(c1ccccc1)c1ccccc1] |
| 34 | 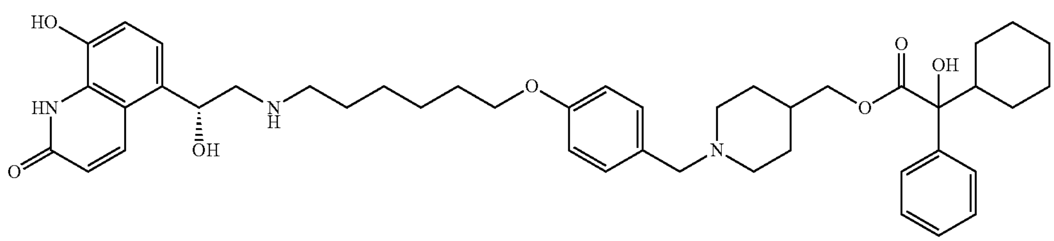 [SMILES: O=C(OCC1CCN(Cc2ccc(OCCCCCCNC[C@H](O)c3ccc(O)c4[nH]c(=O)ccc34)cc2)CC1)C(O)(c1ccccc1)C1CCCCC1] |
| 35 | 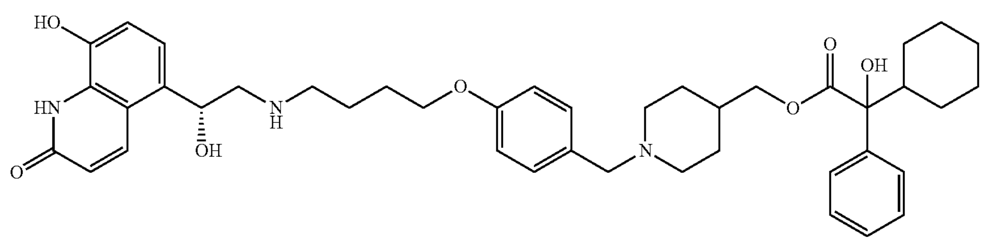 [SMILES: O=C(OCC1CCN(Cc2ccc(OCCCCNC[C@H](O)c3ccc(O)c4[nH]c(=O)ccc34)cc2)CC1)C(O)(c1ccccc1)C1CCCCC1] |

| Compound/ Example | Structure |
|---|---|
| 36 | 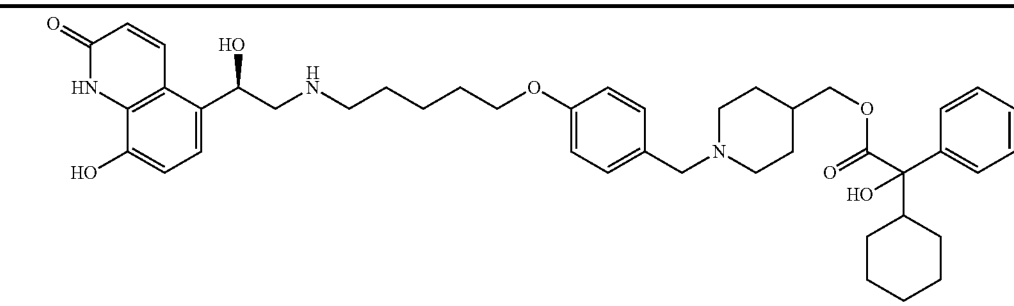 |
| 37 | 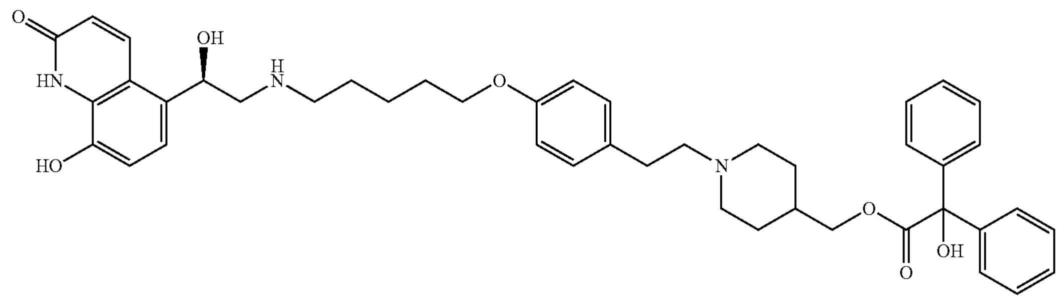 [SMILES: O=C(OCC1CCN(CCc2ccc(OCCCCCNC[C@H](O)c3ccc(O)c4[nH]c(=O)ccc34)cc2)CC1)C(O)(c1ccccc1)c1ccccc1] |

In the following table, the analytical characterization of compounds 1 to 37 is reported. Regarding the NMR data, in CDOD₃, all the exchange protons are not visible

| Compound/ Example | LC R_t time (min) | LC purity (%) | LCMS/ HPLC method | NMR data |
|---|---|---|---|---|
| 1 | 2.52 | 98.29 | A | ¹H NMR (400 MHz, CD₃OD): δ 8.58 (s, 2 H), 8.40 (d, J = 9.8 Hz, 1 H), 7.66-7.61 (m, 2 H), 7.37-7.22 (m, 4 H), 7.03 (d, J = 8.1 Hz, 1 H), 6.69 (d, J = 9.8 Hz, 1 H), 5.43-5.35 (m, 1 H), 4.02 (d, J = 6.2 Hz, 2 H), 3.28-3.13 (m, 4 H), 3.06-2.97 (m, 2 H), 2.73-2.65 (m, 2 H), 2.49-2.36 (m, 2 H), 2.38-2.28 (m, 1 H), 1.87-1.59 (m, 10 H), 1.54-1.03 (m, 20 H) |
| 2 | 7.21¹ | 98.19 | B | ¹H NMR (400 MHz, CD₃OD): δ 8.58 (s, 2 H), 8.42 (d, J = 9.9 Hz, 1 H), 7.56 (d, J = 7.8 Hz, 2 H), 7.39-7.24 (m, 4 H), 7.07 (d, J = 8.2 Hz, 1 H), 6.73 (d, J = 9.8 Hz, 1 H), 5.47-5.39 (m, 1 H), 4.10-3.99 (m, 2 H), 3.42 (d, J = 11.3 Hz, 3 H), 3.25 (d, J = 6.6 Hz, 2 H), 3.12-3.03 (m, 2 H), 2.95-2.86 (m, 2 H), 2.78-2.66 (m, 2 H), 2.25-2.15 (m, 1 H), 2.11-1.98 (m, 1 H), 1.91 (t, J = 7.0 Hz, 3 H), 1.87-1.68 (m, 8 H), 1.59-1.45 (m, 2 H), 1.41 (s, 10 H). |
| 3 | 10.63¹ | 92.39 | B | ¹H NMR (400 MHz, CD₃OD): δ 8.60 (s, 1 H), 8.41 (d, 1 H), 7.69-7.64 (m, 2 H), 7.39-7.24 (m, 4 H), 7.07-7.00 (m, 1 H), 6.71 (d, 1 H), 5.43-5.36 (m, 1 H), 4.08-3.98 (m, 2 H), 3.22-3.15 (m, 4 H), 3.10-2.97 (m, 3 H), 2.69-2.61 (m, 2 H), 2.43-2.30 (m, 2 H), 1.81-1.58 (m, 12 H), 1.82-1.05 (m, 15 H). |
| 4 | 7.17¹ | 96.41 | B | ¹H NMR (400 MHz, CD₃OD): δ 8.59 (s, 1 H), 8.42 (d, J = 9.8 Hz, 1 H), 7.46-7.29 (m, 11 H), 7.06 (d, J = 8.1 Hz, 1 H), 6.74-6.65 (m, 1 H), 5.46-5.38 (m, 1 H), 4.14 (d, J = 6.4 Hz, 2 H), 3.27-3.17 (m, 4 H), 3.08-2.99 (m, 2 H), 2.77-2.65 (m, 2 H), 2.53-2.40 (m, 2 H), 1.91-1.53 (m, 7 H), 1.39 (s, 12 H). |
| 5 | 7.30¹ | 97.3 | B | ¹H NMR (400 MHz, CD₃OD): δ 8.40 (d, J = 9.8 Hz, 1 H), 7.66-7.61 (m, 2 H), 7.39-7.26 (m, 1 H), 7.24-7.16 (m, 6 H), 6.95 (d, J = 8.2 Hz, 1 H), 6.66 (d, J = 9.8 Hz, 1 H), 5.25 (dd, J = 9.0, 3.9 Hz, 1 H), 4.00 (dd, J = 10.8, 6.4 Hz, 1 H), 3.92 (dd, J = 10.8, 6.3 Hz, 1 H), 3.60 (d, J = 13.8 Hz, 1 H), 3.25 (d, J = 13.8 Hz, 1 H), 3.01-2.86 (m, 4 H), 2.79-2.70 (m, 2 H), 2.36 (t, J = 7.9 Hz, 2 H), 2.00-1.89 (m, 2 H), 1.56 (d, J = 18.5 Hz, 8 H), 1.42-1.13 (m, 14 H). |
| 6 | 9.87¹ | 97.73 | B | ¹H NMR (400 MHz, CD₃OD): δ 8.57 (s, 1 H), 8.41 (d, 1 H), 7.65-7.63 (m, 2 H), 7.37-7.25 (m, 4 H), 7.03-7.01 (m, 1 H), 6.69 (d, 1 H), 5.39-5.35 (m, 1 H), 4.02-3.97 (m, 2 H), 3.34-3.14 (m, 4 H), 2.99-2.96 (m, 2 H), 2.59-2.54 (m, 3 H), 2.30-2.24 (m, 2 H), 1.80-1.57 (m, 12 H), 1.55-1.23 (m, 19 H). |
| 7 | 7.45¹ | 99.36 | B | ¹H NMR (400 MHz, CD₃OD): δ 8.57 (s, 1 H), 8.39 (d, J = 9.9 Hz, 1 H), 7.65 (dd, J = 8.0, 1.3 Hz, 2 H), 7.39-7.32 (m, 2 H), 7.31-7.25 (m, 2 H), 7.04 (d, J = 8.2 Hz, 1 H), 6.71 (d, J = 9.8 Hz, 1 H), 5.38 (dd, J = 8.2, 5.2 Hz, 1 H), 3.96 (s, 2 H), 3.21-3.13 (m, 2 H), 3.06-2.97 (m, 2 H), 2.79-2.65 (m, 4 H), 1.75-1.56 (m, 9 H), 1.56-1.42 (m, 6 H), 1.39 (s, 11 H), 1.32-1.06 (m, 5 H), 1.01 (s, 3 H). |
| 8 | 2.67 | 97.39 | B | ¹H NMR (400 MHz, CD₃OD): δ 8.40 (d, J = 9.8 Hz, 1 H), 7.34-7.19 (m, 6 H), 6.95 (d, J = 8.2 Hz, 1 H), 6.66 (d, J = 9.8 Hz, 1 H), 5.25 (dd, J = 9.1, 3.9 Hz, 1 |

| Compound/Example | LC R_t time (min) | LC purity (%) | LCMS/HPLC method | NMR data |
|---|---|---|---|---|
| | | | | H), 3.93 (d, J = 5.9 Hz, 2 H), 3.27 (d, J = 10.8 Hz, 1 H), 3.01-2.87 (m, 4 H), 2.79-2.71 (m, 2 H), 2.40-2.32 (m, 2 H), 2.08-1.94 (m, 3 H), 1.80 (t, J = 15.1 Hz, 2 H), 1.69-1.47 (m, 9 H), 1.39-1.14 (m, 19 H), 0.85-0.75 (m, 1 H). |
| 9 | 7.34[1] | 96.3 | B | $^1$H NMR (400 MHz, CD$_3$OD): δ 8.57 (s, 2 H), 8.39 (d, 1 H), 7.34-7.28 (m, 2 H), 7.13 (dd, 1 H), 7.04 (d, 1 H), 7.00 (dd, 1 H), 6.71 (d, 1 H), 5.39 (t, 1 H), 4.08 (d, 2 H), 3.31-3.27 (m, 2 H), 3.23-3.19 (m, 2 H), 3.04 (t, 2 H), 2.79-2.73 (m, 2 H), 2.59-2.49 (m, 2 H), 2.21-2.12 (m, 1 H), 1.94-1.60 (m, 9 H), 1.60-1.13 (m, 20 H). |
| 10 | 7.10[1] | 97.81 | A | $^1$H NMR (400 MHz, CD$_3$OD): δ 8.56 (s, 2 H), 8.39 (d, J = 9.9 Hz, 1 H), 7.44-7.28 (m, 8 H), 7.09 (dd, J = 5.0, 1.4 Hz, 1 H), 7.05 (d, J = 8.2 Hz, 1 H), 6.71 (d, J = 9.8 Hz, 1 H), 5.44-5.37 (m, 1 H), 4.18-4.10 (m, 2 H), 3.41-3.30 (m, 2 H), 3.22 (d, J = 6.6 Hz, 2 H), 3.10-3.02 (m, 2 H), 2.85 (t, J = 7.9 Hz, 2 H), 2.71-2.58 (m, 2 H), 1.90 (t, J = 9.5 Hz, 1 H), 1.83-1.57 (m, 4 H), 1.56-1.25 (m, 14 H). |
| 11 | 6.59[1] | 99.06 | B | $^1$H NMR (400 MHz, CD$_3$OD): δ 8.53 (s, 2 H), 8.48-8.36 (m, 1 H), 7.44-7.29 (m, 11 H), 7.05 (d, J = 8.2 Hz, 1 H), 6.70 (d, J = 9.8 Hz, 1 H), 5.44 (dd, J = 8.6, 4.8 Hz, 1 H), 4.15 (d, J = 6.3 Hz, 2 H), 3.46 (d, J = 12.3 Hz, 2 H), 3.08 (t, J = 8.0 Hz, 2 H), 3.02-2.95 (m, 2 H), 2.90-2.78 (m, 2 H), 1.98-1.90 (m, 1 H), 1.83-1.67 (m, 6 H), 1.65-1.30 (s, 10 H). |
| 12 | 7.07[1] | 96.78 | B | $^1$H NMR (400 MHz, CD$_3$OD): δ 8.55 (s, 2 H), 8.39 (d, J = 9.8 Hz, 1 H), 7.40 (d, J = 5.1 Hz, 2 H), 7.30 (d, J = 8.2 Hz, 1 H), 7.16 (d, J = 3.6 Hz, 2 H), 7.08-6.96 (m, 3 H), 6.71 (d, J = 9.8 Hz, 1 H), 5.44-5.38 (m, 1 H), 4.17 (d, J = 6.4 Hz, 2 H), 3.39 (m, 2 H), 3.23 (d, J = 6.7 Hz, 2 H), 3.10-3.01 (m, 2 H), 2.93-2.85 (m, 2 H), 2.77-2.65 (m, 2 H), 1.96 (s, 1 H), 1.91-1.63 (m, 4 H), 1.61-1.28 (m, 14 H). |
| 13 | 7.38[1] | 97.95 | B | $^1$H NMR (400 MHz, CD$_3$OD): δ 8.58 (s, 2 H), 8.40 (d, J = 9.9 Hz, 1 H), 7.64 (dd, J = 7.9, 1.2 Hz, 2 H), 7.38-7.23 (m, 4 H), 7.05 (d, J = 8.2 Hz, 1 H), 6.70 (d, J = 9.8 Hz, 1 H), 5.45-5.38 (m, 1 H), 4.04 (d, J = 6.2 Hz, 2 H), 3.40 (d, J = 11.8 Hz, 2 H), 3.27-3.16 (m, 2 H), 3.10-3.02 (m, 2 H), 2.92-2.84 (m, 2 H), 2.74-2.63 (m, 2 H), 2.37-2.28 (m, 1 H), 1.86-1.63 (m, 10 H), 1.67-1.29 (m, 15 H), 1.23-1.05 (m, 4 H). |
| 14 | 7.40[1] | 99.67 | B | $^1$H NMR (400 MHz, CD$_3$OD): δ 8.58 (s, 1 H), 8.40 (d, J = 9.8 Hz, 1 H), 7.64 (dd, J = 7.9, 1.2 Hz, 2 H), 7.38-7.31 (m, 2 H), 7.30-7.23 (m, 2 H), 7.04 (d, J = 8.2 Hz, 1 H), 6.69 (d, J = 9.8 Hz, 1 H), 5.43-5.36 (m, 1 H), 4.06-3.99 (m, 2 H), 3.20 (d, J = 6.6 Hz, 2 H), 3.03 (t, J = 7.8 Hz, 2 H), 2.76-2.68 (m, 2 H), 2.53-2.40 (m, 2 H), 2.38-2.27 (m, 1 H), 1.87-1.62 (m, 10 H), 1.60-1.30 (m, 15 H), 1.23-1.02 (m, 4 H). |
| 15 | 8.43[1] | 98.19 | B | $^1$H NMR (400 MHz, CD$_3$OD): δ 8.55 (s, 2 H), 8.39 (d, J = 9.9 Hz, 1 H), 7.50-7.45 (m, 2 H), 7.42 (dd, J = 5.1, 1.3 Hz, 1 H), 7.40-7.30 (m, 4 H), 7.12-7.08 (m, 1 H), 7.07-6.99 (m, 2 H), 6.71 (d, J = 9.8 Hz, 1 H), 5.45-5.37 (m, 1 H), 4.20-4.10 (m, 2 H), 3.39-3.31 (m, 12 H), 3.23 (d, J = 6.7 Hz, 2 H), 3.10-3.02 (m, 2 H), 2.91-2.83 (m, 2 H), 2.74-2.63 (m, 2 H), 1.93 (t, J = 10.3 Hz, 1 H), 1.87-1.61 (m, 4 H), 1.60-1.28 (m, 14 H). |
| 16 | 7.60[1] | 96.25 | B | $^1$H NMR (400 MHz, CD$_3$OD): δ 8.58 (s, 1 H), 8.45-8.35 (m, 1 H), 7.66-7.61 (m, 2 H), 7.38-7.23 (m, 4 H), 7.07-6.99 (m, 1 H), 6.70 (dd, J = 9.8, 4.2 Hz, 1 H), 5.42 (q, J = 6.7 Hz, 1 H), 4.04 (t, J = 6.2 Hz, 2 H), 3.32-3.22 (m, 2 H), 3.21 (d, J = 6.7 Hz, 2 H), 3.04 (t, J = 7.9 Hz, 2 H), 2.81-2.72 (m, 2 H), 2.61-2.47 (m, 2 H), 2.37-2.28 (m, 1 H), 1.95-1.62 (m, 10 H), 1.61-1.31 (m, 13 H), 1.23-1.03 (m, 4 H). |
| 17 | 7.52[1] | 97.31 | B | $^1$H NMR (400 MHz, CD$_3$OD): δ 8.58 (s, 1 H), 8.45-8.36 (m, 1 H), 7.66-7.61 (m, 2 H), 7.38-7.23 (m, 4 H), 7.04 (d, J = 8.2 Hz, 1 H), 6.70 (t, J = 9.8 Hz, 1 H), 5.42 (q, J = 6.7 Hz, 1 H), 4.05 (dd, J = 17.2, 6.2 Hz, 2 H), 3.32-3.22 (m, 2 H), 3.21 (d, J = 6.7 Hz, 2 H), 3.12-3.00 (m, 2 H), 2.83-2.74 (m, 2 H), 2.63-2.49 (m, 2 H), 2.37-2.28 (m, 1 H), 1.93-1.65 (m, 10 H), 1.57-1.40 (m, 11 H), 1.22-1.03 (m, 4 H). |
| 18 | 7.16[1] | 97.22 | B | $^1$H NMR (400 MHz, CD$_3$OD): δ 8.56 (s, 2 H), 8.47-8.35 (m, 1 H), 7.64 (dd, J = 7.9, 1.3 Hz, 2 H), 7.37-7.22 (m, 4 H), 7.05 (d, J = 8.2 Hz, 1 H), 6.74-6.65 (m, 1 H), 5.44-5.37 (m, 1 H), 4.09-4.00 (m, 2 H), 3.34-3.31 (m, 2 H), 3.22 (d, J = 6.7 Hz, 2 H), 3.13-3.03 (m, 2 H), 2.84-2.76 (m, 2 H), 2.61-2.48 (m, 2 H), 2.37-2.28 (m, 1 H), 1.85-1.64 (m, 10 H), 1.54-1.41 (m, 7 H), 1.23-1.03 (m, 4 H). |
| 19 | 7.20[1] | 99.1 | B | $^1$H NMR (400 MHz, CD$_3$OD): δ 8.58 (s, 2 H), 8.40 (d, J = 9.9 Hz, 1 H), 7.66-7.61 (m, 2 H), 7.38-7.23 (m, 4 H), 7.05 (d, J = 8.2 Hz, 1 H), 6.70 (d, J = 9.8 Hz, 1 H), 5.42 (t, J = 6.7 Hz, 1 H), 4.04 (t, J = 5.9 Hz, 2 H), 3.32-3.22 (m, 2 H), 3.25-3.19 (m, 2 H), 3.06 (t, J = 7.9 Hz, 2 H), 2.83 (t, J = 7.9 Hz, 2 H), 2.61 (t, J = 12.3 Hz, 2 H), 2.38-2.27 (m, 1 H), 1.85-1.64 (m, 10 H), 1.57-1.38 (m, 9 H), 1.22-1.03 (m, 4 H). |
| 20 | 7.42 | 95.1 | B | $^1$H NMR (400 MHz, CD$_3$OD): δ 8.57 (s, 1 H), 8.39 (d, J = 9.9 Hz, 1 H), 7.35-7.25 (m, 11 H), 7.09-7.00 (m, 2 H), 6.69 (d, J = 9.8 Hz, 1 H), 5.44-5.37 (m, 1 H), 4.42 (s, 2 H), 4.08 (d, J = 6.3 Hz, 2 H), 3.27 (d, J = 12.1 Hz, 2H), 3.20 (d, J = 6.7 Hz, 2 H), 3.07-2.99 (m, 2 H), 2.79-2.72 (m, 2 H), 2.59-2.47 (m, 2 H), 1.90-1.53 (m, 9 H), 1.75-1.00 (m, 11 H). |
| 21 | 7.73 | 94.19 | B | $^1$H NMR (400 MHz, CD$_3$OD): δ 8.56 (s, 2 H), 8.39 (d, J = 9.9 Hz, 1 H), 7.30 (d, J = 8.2 Hz, 1 H), 7.05 (t, J = 6.9 Hz, 1 H), 6.70 (d, J = 9.8 Hz, 1 H), 5.42-5.35 (m, 1 H), 4.05 (d, J = 5.7 Hz, 2 H), 3.37 (d, J = 9.7 Hz, 2 H), 3.20 (t, J = 6.7 Hz, |

| Compound/ Example | LC R$_t$ time (min) | LC purity (%) | LCMS/ HPLC method | NMR data |
|---|---|---|---|---|
| | | | | 2 H), 3.08-2.99 (m, 2 H), 2.83-2.75 (m, 2 H), 2.66-2.54 (m, 2 H), 1.97-1.62 (m, 15 H), 1.62-1.08 (m, 24 H), 0.94 (ddd, J = 24.7, 12.4, 3.2 Hz, 2 H). |
| 22 | 8.01 | 93.72 | B | $^1$H NMR (400 MHz, CD$_3$OD): δ 8.55 (s, 2 H), 8.39 (d, J = 9.9 Hz, 1 H), 7.32-7.18 (m, 16 H), 7.04 (d, J = 8.2 Hz, 1 H), 6.70 (d, J = 9.8 Hz, 1 H), 5.43-5.37 (m, 1 H), 3.82 (s, 2 H), 3.68 (d, J = 6.0 Hz, 2 H), 3.30 (m, 2 H), 3.23-3.17 (m, 2 H), 3.09-3.00 (m, 2 H), 2.89-2.81 (m, 2 H), 2.63-2.51 (m, 2 H), 1.79-1.45 (m, 5 H), 1.41-1.19 (m, 14 H). |
| 23 | 7.08 | 97.36 | B | $^1$H NMR (400 MHz, CD$_3$OD): δ 8.57 (s, 1 H), 8.39 (d, J = 10 Hz, 1 H), 7.40-7.26 (m, 11 H), 7.03 (d, J = 8.4 Hz, 1 H), 6.70 (d, J = 10 Hz, 1 H), 5.41-5.36 (m, 1 H), 4.08 (d, J = 6.4 Hz, 2 H), 3.28-3.16 (m, 4 H), 3.04-2.98 (m, 2 H), 2.75-2.69 (m, 2 H), 2.53-2.44 (m, 2 H), 2.08 (s, 3 H), 1.88-1.58 (m, 5 H), 1.47-1.30 (m, 14 H). |
| 24 | 2.02 | 98.52 | A | $^1$H NMR (400 MHz, CD$_3$OD): δ 8.39 (d, J = 10 Hz, 1 H), 7.43-7.32 (m, 9 H), 7.20 (d, J = 8.4 Hz, 1 H), 6.94 (d, J = 8.4 Hz, 1 H), 6.65 (d, J = 10 Hz, 1 H), 5.24 (dd, J = 9, 3.8 Hz, 1 H), 4.09 (d, J = 10 Hz, 2 H), 3.05-2.83 (m, 4 H), 2.80-2.66 (m, 2 H), 2.41-2.29 (m, 2 H), 2.01-1.88 (m, 2 H), 1.69-1.46 (m, 6 H), 1.55-0.98 (m, 13 H). |
| 25 | 2.50 | 98.28 | A | $^1$H NMR (400 MHz, CD$_3$OD): δ 8.46 (s, 3 H), 8.40 (d, J = 9.9 Hz, 1 H), 7.42-7.36 (m, 2 H), 7.31 (d, J = 8.1 Hz, 1 H), 7.21 (dd, J = 4.9, 1.4 Hz, 1 H), 7.05 (d, J = 8.1 Hz, 1 H), 6.71 (d, J = 9.6 Hz, 1 H), 5.42 (s, 1 H), 4.13-4.02 (m, 2 H), 3.59-3.49 (m, 2 H), 3.27-3.22 (m, 2 H), 3.12-3.01 (m, 4 H), 2.97-2.86 (m, 2 H), 2.26-2.17 (m, 1 H), 2.07-1.07 (m, 29 H). |
| 26 | 7.14 | 97.26 | B | $^1$H NMR (400 MHz, CD$_3$OD): δ 8.39 (d, J = 9.8 Hz, 1 H), 7.45-7.20 (m, 7 H), 7.00-6.85 (m, 4 H), 6.65 (d, J = 9.8 Hz, 1 H), 5.25 (dd, J = 9.1, 3.9 Hz, 1 H), 4.08 (d, J = 6.4 Hz, 2 H), 3.86-3.72 (m, 3 H), 3.02-2.88 (m, 4 H), 2.82-2.69 (m, 2 H), 2.38-2.30 (m, 2 H), 2.02-1.90 (m, 2 H), 1.71-1.47 (m, 6 H), 1.45-1.08 (m, 13 H). |
| 27 | 7.20 | 98.37 | B | $^1$H NMR (400 MHz, CD$_3$OD): δ 8.56 (s, 2H), 8.40 (d, J = 10 Hz, 1H), 7.46-7.29 (m, 8H), 7.11-7.03 (m, 3H), 6.71 (d, J = 10 Hz, 1H), 5.42-5.39 (m, 1H), 4.14 (d, J = 6.8 Hz, 2H), 3.32-3.29 (m, 2H), 3.22 (d, J = 6.8 Hz, 2H), 3.06 (t, J = 8 Hz, 2H), 2.82-2.78 (m, 2H), 2.61-2.55 (m, 2H), 1.88-1.81 (m, 1H), 1.75-1.65 (m, 6H), 1.46-1.38 (m, 12H) |
| 28 | 6.92 | 97.26 | B | $^1$H NMR (400 MHz, CD$_3$OD): δ 8.50 (s, 3 H), 8.40 (d, J = 10 Hz, 1 H), 7.63 (d, J = 7.6 Hz, 2 H), 7.38-7.25 (m, 4 H), 7.04 (d, J = 8 Hz, 1 H), 6.70 (d, J = 10 Hz, 1 H), 5.34 (m, 1 H), 4.05 (d, J = 6.4 Hz, 2 H), 3.53-3.45 (m, 2 H), 3.36-3.23 (m, 2 H), 3.16-3.07 (m, 3 H), 3.04-2.97 (m, 2 H), 2.91-2.80 (m, 2 H), 2.73-2.67 (m, 2 H), 2.56-2.44 (m, 2 H), 2.38-2.28 (m, 1 H), 2.22-2.09 (m, 2 H), 2.03-1.92 (m, 1 H), 1.92-1.29 (m, 20 H), 1.28-1.06 (m, 4 H). |
| 29 | 2.59 | 99.16 | A | $^1$H NMR (400 MHz, CD$_3$OD): δ 8.57 (s, 2 H); 7.68-7.64 (m, 2 H); 7.40-7.34 (m, 2 H); 7.32-7.26 (m, 1 H); 6.95 (d, J = 8.3 Hz, 1 H); 6.79 (d, J = 8.2 Hz, 1 H); 4.06 (d, J = 6.3 Hz, 2 H); 3.47-3.38 (m, 2 H); 3.28-3.20 (m, 2 H); 3.07-2.88 (m, 6 H); 2.79-2.67 (m, 2 H); 2.38-2.29 (m, 1 H); 2.01-1.78 (m, 4 H); 1.76-1.64 (m, 6 H); 1.67-1.32 (m, 16 H); 1.24-1.07 (m, 4 H). |
| 30 | 7.26 | 92 | B | (CD$_3$OD): δ 8.49 (s, 2 H); 8.33 (d, J = 9.8 Hz, 1 H); 7.60-7.55 (m, 2 H); 7.32-7.17 (m, 4 H); 6.99 (d, J = 8.1 Hz, 1 H); 6.65 (d, J = 9.8 Hz, 1 H); 5.41-5.30 (m, 2 H); 3.96 (d, J = 6.2 Hz, 2 H); 3.86 (s, 2 H); 3.56-3.48 (m, 2 H); 3.20 (d, J = 7.5 Hz, 6 H); 2.73-2.64 (m, 2 H); 2.47-2.22 (m, 5 H); 2.09-1.83 (m, 2 H); 1.84-1.58 (m, 8 H); 1.48-1.26 (m, 6 H); 1.17-0.96 (m, 4 H). |
| 31 | 2.25 | 93 | A | (CD$_3$OD): δ 8.38 (s, 2 H); 8.30-8.21 (m, 1 H); 7.29-7.14 (m, 13 H); 6.90 (d, J = 8.2 Hz, 1 H); 6.83 (d, J = 8.4 Hz, 2 H); 6.55 (d, J = 9.8 Hz, 1 H); 5.31-5.24 (m, 1 H); 3.98 (d, J = 6.4 Hz, 2 H); 3.91-3.86 (m, 4 H); 3.16-3.06 (m, 4 H); 3.03-2.92 (m, 2 H); 2.62-2.49 (m, 2 H); 1.77-1.54 (m, 7 H); 1.50-1.20 (m, 6 H). |
| 32 | 2.41 | 96 | A | (CD$_3$OD): δ 8.55 (s, 2 H); 8.39 (d, J = 9.9 Hz, 1 H); 7.42-7.28 (m, 13 H); 7.05 (d, J = 8.2 Hz, 1 H); 6.97 (d, J = 8.4 Hz, 2 H); 6.67 (d, J = 9.8 Hz, 1 H); 5.46-5.39 (m, 1 H); 4.13-4.04 (m, 4 H); 3.92 (s, 2 H); 3.27-3.14 (m, 6 H); 2.63-2.51 (m, 2 H); 1.98-1.80 (m, 5 H); 1.74-1.63 (m, 2 H); 1.47-1.33 (m, 2 H). |
| 33 | 7.16 | 96 | B | (CD$_3$OD): δ 8.56 (s, 2 H); 8.39 (d, J = 9.9 Hz, 1 H); 7.43-7.28 (m, 13 H); 7.04 (d, J = 8.2 Hz, 1 H); 6.94 (d, J = 8.4 Hz, 2 H); 6.68 (d, J = 9.8 Hz, 1 H); 5.45-5.38 (m, 1 H); 4.11 (d, J = 6.4 Hz, 2 H); 4.04 (t, J = 6.1 Hz, 2 H); 3.86 (s, 2 H); 3.26-3.20 (m, 2 H); 3.19-3.06 (m, 4 H); 2.56-2.44 (m, 2 H); 1.92-1.77 (m, 5 H); 1.71-1.56 (m, 4 H); 1.43-1.30 (m, 2 H). |
| 34 | 9.01 | 95 | B | (CD$_3$OD): δ 8.59 (s, 2 H); 8.39 (d, J = 9.9 Hz, 1 H); 7.65-7.60 (m, 2 H); 7.35-7.22 (m, 6 H); 7.04 (d, J = 8.2 Hz, 1 H); 6.94 (d, J = 8.4 Hz, 2 H); 6.76-6.62 (m, 1 H); 5.47-5.41 (m, 1 H); 4.05-3.95 (m, 4 H); 3.84 (s, 2 H); 3.26-3.13 (m, 4 H); 3.13-3.05 (m, 2 H); 2.53-2.40 (m, 2 H); 2.36-2.26 (m, 1 H); 1.84-1.30 (m, 19 H); 1.22-1.01 (m, 4 H). |
| 35 | 8.81 | 93 | B | (CD$_3$OD): δ 8.58 (s, 2 H); 8.39 (d, J = 9.9 Hz, 1 H); 7.65-7.60 (m, 2 H); 7.39-7.20 (m, 6 H); 7.08-7.00 (m, 1 H); 6.98 (d, J = 8.3 Hz, 2 H); 6.66 (d, J = 9.8 Hz, 1 H); 5.46 (dd, J = 9.0, 4.3 Hz, 1 H); 4.09-3.98 (m, 6 H); 3.34-3.16 (m, 6 H); 2.74-2.62 (m, 2 H); 2.36-2.26 (m, 1 H); 2.01-1.84 (m, 5 H); 1.82-1.71 (m, 3 H); 1.66 (d, J = 10.2 Hz, 2 H); 1.55-1.26 (m, 5 H); 1.24-1.01 (m, 4 H). |
| 36 | 7.38 | 98 | B | (CD$_3$OD): δ 8.39 (d, J = 9.8 Hz, 1 H); 7.65-7.60 (m, 2 H); 7.36-7.30 (m, 2 H); 7.29-7.20 (m, 4 H); 6.96 (d, J = 8.2 Hz, 1 H); 6.91-6.84 (m, 2 H); |

-continued

| Compound/Example | LC R$_t$ time (min) | LC purity (%) | LCMS/HPLC method | NMR data |
|---|---|---|---|---|
| 37 | 7.19 | 99 | B | 6.66 (d, J = 9.8 Hz, 1 H); 5.26 (dd, J = 9.1, 3.8 Hz, 1 H); 4.04-3.92 (m, 4 H); 3.46 (s, 2 H); 3.02-2.86 (m, 4 H); 2.85-2.74 (m, 2 H); 2.36-2.25 (m, 1 H); 2.04-1.91 (m, 2 H); 1.89-1.77 (m, 3 H); 1.73-1.04 (m, 18 H). (CD$_3$OD): δ 8.56 (s, 2 H); 8.38 (d, J = 9.9 Hz, 1 H); 7.43-7.27 (m, 11 H); 7.15 (d, J = 8.4 Hz, 2 H); 7.05 (d, J = 8.2 Hz, 1 H); 6.86 (d, J = 8.4 Hz, 2 H); 6.72-6.62 (m, 1 H); 5.47-5.41 (m, 1 H); 4.14 (d, J = 6.4 Hz, 2 H); 4.02-3.95 (m, 2 H); 3.47-3.37 (m, 2 H); 3.28-3.18 (m, 2 H); 3.16-3.01 (m, 4 H); 2.97-2.86 (m, 2 H); 2.81-2.65 (m, 2 H); 1.93-1.71 (m, 7 H); 1.65-1.54 (m, 2 H); 1.54-1.42 (m, 2 H). |

HPLC data
Method:
A IS 10 cm_ESCI_Formic_MeCN
B IS 15 cm_Formic_ASCENTIS_HPLC_CH$_3$CN
Legend
* NMR
s = singlet
d = doublet
t = triplet
q = quartet
dd = doublet of doublets
m = multiplet
br = broad Biological Characterization Example 38

M3 Receptor radioligand binding assay

Human M3 receptor membranes (15 ug/well) from Perkin Elmer were incubated with 0.52 nM Scopolamine Methyl Chloride, [N-methyl-3H] with or without test compounds, or a saturating concentration of Atropine (5 μM) for the determination of non-specific binding. The assay was carried out in 96-well polypropylene plates in a volume of 250 ul. The assay buffer used was 50 mM Tris-HCl, 154 mM NaCl (pH 7.4). The final assay concentration of DMSO was 0.5% (v/v). The plates were sealed and incubated for 2 hours at room temperature on an orbital shaker (slow speed). Membranes were harvested onto 96-well unifilter GF/C filter plates pre-treated with 0.5% polyethyleneimine (v/v), using a filter manifold, washed four times with 200 ul of assay buffer. The plates were dried before addition of 50 μl of microscint-0, sealed then read in a Trilux Microbeta scintillation counter. IC50 values are determined from competition curves using a non-linear curve fitting program. Ki values were calculated from IC50 values by the Cheng and Prusoff equation.

The Ki values of the tested compounds are less than 10 nM.

Example 39

β2 Adrenoceptor Radioligand Binding Assay

Human β$_2$ adrenoceptor membranes (7.5 ug/well) from Perkin Elmer were incubated with 0.3 nM 125-I Cyanopindolol with or without test compounds, or a saturating concentration of s-propranolol (2 μM) for the determination of non-specific binding. The assay was carried out in 96-well polypropylene plates in a volume of 200 ul. The assay buffer used was 25 mM HEPES, 0.5% BSA (w/v), 1 mM EDTA, 0.02% ascorbic acid (v/v), (pH 7.4). The final assay concentration of DMSO was 0.5% (v/v). The plates were sealed and incubated for 1 hour at room temperature on an orbital shaker (slow speed). Membranes were harvested onto 96-well unifilter GF/C filter plates pre-treated with 0.5% polyethyleneimine (v/v), using a filter manifold, washed six times with 200 ul of wash buffer containing 10 mM HEPES and 500 mM NaCl. The plates were dried before addition of 50 μl of microscint-0, sealed then read in a Trilux Microbeta scintillation counter. IC50 values are determined from competition curves using a non-linear curve fitting program. Ki values were calculated from IC50 values by the Cheng and Prusoff equation.

The Ki values of the tested compounds are less than 10 Nm.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

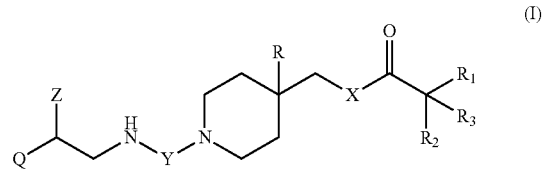

wherein:
Q is a group of formula Q1, Q2, Q3, Q4, Q5, or Q6:

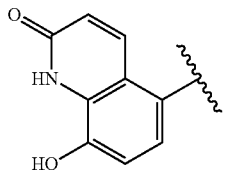
Q1

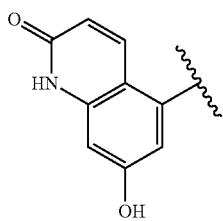
Q2

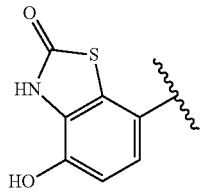
Q3

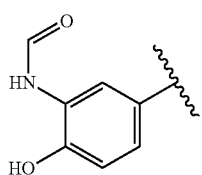
Q4

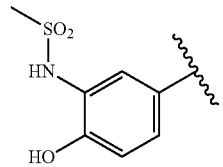
Q5

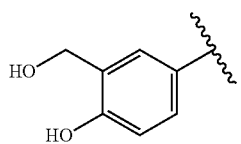
Q6

Z is H or OH;
Y is —(CH$_2$)$_n$— wherein n is an integer of 1 to 12 or is a divalent group of formula Y1:

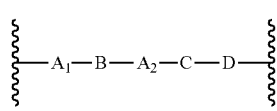
Y1 wherein:
A1 and A2 are, each independently, absent or are selected from the group consisting of (C$_1$-C$_6$)alkylene, (C$_3$-C$_8$)cycloalkylene, and (C$_3$-C$_8$)heterocycloalkylene;
B is absent or is selected from the group consisting of (C$_3$-C$_8$)cycloalkylene, (C$_3$-C$_8$)heterocycloalkylene, arylene, and heteroarylene or is a group of formula B1

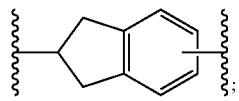
B1

C is absent or is selected from the group consisting of —O—, —OCO—, —C(O)O—, —S—, —S(O)—, —S(O)$_2$—, and —N(R$_4$)— or is one of the following groups C1-C10:

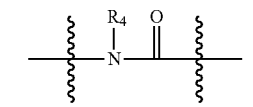
C1

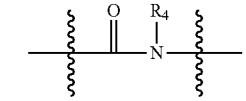
C2

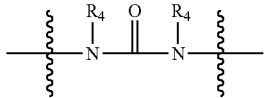
C3

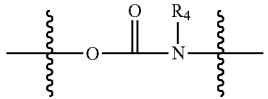
C4

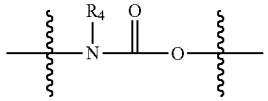
C5

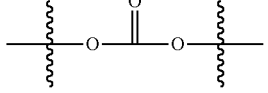
C6

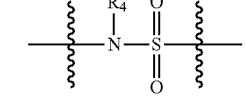
C7

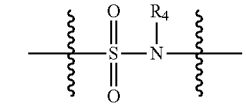
C8

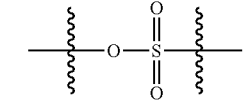
C9

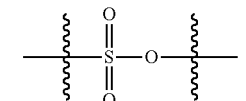
C10 wherein R$_4$ is H or is selected from the group consisting of (C$_1$-C$_8$)alkyl, (C$_3$-C$_8$)cycloalkyl, (C$_3$-C$_8$)heterocloalkyl, aryl, and heteroaryl;
D is selected from the group consisting of (C$_1$-C$_{12}$)alkylene, (C$_2$-C$_{12}$)alkenylene, and (C$_2$-C$_6$)alkynylene, optionally substituted by one or more (C$_1$-C$_6$)alkyl;

R is —H or (C₁-C₄)alkyl;

X is —O— or —S—;

R₁ is H or is selected from the group consisting of (C₃-C₈)cycloalkyl, aryl, heteroaryl, aryl(C₁-C₆)alkyl, heteroaryl(C₁-C₆)alkyl, and (C₃-C₈)cycloalkyl(C₁-C₆)alkyl, optionally substituted by one or more (C₁-C₄)alkoxy;

R₂ is selected from the group consisting of (C₃-C₈)cycloalkyl, aryl, heteroaryl, aryl(C₁-C₆)alkyl, heteroaryl(C₁-C₆)alkyl, and (C₃-C₈)cycloalkyl(C₁-C₆)alkyl, optionally substituted by one or more halogen atoms or (C₁-C₄)alkoxy;

R₃ is H or is selected from the group consisting of —OH, hydroxy(C₁-C₆)alkyl, —N(R₅R₆), and —N(R₅)CO(R₆);

R₅ and R₆ are independently H or (C₁-C₆)alkyl;

or a pharmaceutically acceptable salt thereof.

2. A compound or salt according to claim 1, wherein R₁ is H or is selected from the group consisting of (C₃-C₈)cycloalkyl, aryl, heteroaryl, and aryl(C₁-C₆)alkyl; R₂ is selected from the group consisting of (C₃-C₈)cycloalkyl, aryl, heteroaryl, aryl(C₁-C₆)alkyl, heteroaryl(C₁-C₆)alkyl, and (C₃-C₈)cycloalkyl(C₁-C₆)alkyl; R₃ is H or is selected from the group consisting of —OH, hydroxy(C₁-C₆)alkyl, —N(R₅R₆), and —N(R₅)CO(R₆); X is —O— or —S—; and R is —H or (C₁-C₄)alkyl.

3. A compound or salt according to claim 2, wherein R₁ is H or is selected from the group consisting of cyclobutyl, cyclopentyl, phenyl, benzyl, cycloheptyl, thienyl, and cyclohexyl; R₂ is selected from the group consisting of phenyl, thienyl, cyclohexyl, triphenylmethyl, chlorophenyl, methoxyphenyl, and fluorophenyl; R₃ is H or is selected from the group consisting of —OH, —NH₂, —CH₂OH, —NHCOCH₃; X is —O—; and R is H or —CH₃.

4. A compound or salt according to claim 1, wherein Y is —(CH₂)ₙ— wherein n is an integer of 1 to 12 or is a group of formula Y1:

$$\{-A_1-B-A_2-C-D-\}$$ (Y1)

wherein:

A1 and A2 are, each independently, absent or are selected from the group consisting of (C₁-C₆)alkylene, (C₃-C₈)cycloalkylene, and (C₃-C₈)heterocycloalkylene; B is absent or is selected from the group consisting of (C₃-C₈)cycloalkylene, (C₃-C₈)heterocycloalkylene, arylene, and heteroarylene or is a group of formula B1:

(B1)

C is absent or is selected from the group consisting of —O—, —OCO—, —C(O)O—, —S—, —N(R₄)— or is one of the following C1-C10 groups:

(C1) —N(R₄)—C(O)—

(C2) —C(O)—N(R₄)—

(C3) —N(R₄)—C(O)—N(R₄)—

(C4) —O—C(O)—N(R₄)—

(C5) —N(R₄)—C(O)—O—

(C6) —O—C(O)—O—

(C7) —N(R₄)—S(O)₂—

(C8) —S(O)₂—N(R₄)—

(C9) —O—S(O)₂—

(C10) —S(O)₂—O— wherein R₄ is H or is selected from the group consisting of (C₁-C₈)alkyl, (C₃-C₈)cycloalkyl, (C₃-C₈)heterocycloalkyl, aryl, and heteroaryl; D is selected from the group consisting of (C₁-C₁₂)alkylene, (C₂-C₁₂)alkenylene, and (C₂-C₆)alkynylene; Z is —H or —OH and Q is a group of formula Q1, Q2, Q3, Q4, Q5 or Q6:

(Q1)

-continued

Q2
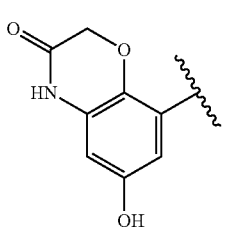

Q3

Q4
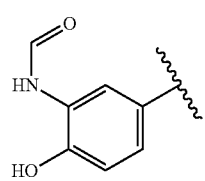

Q5
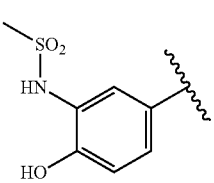

Q6
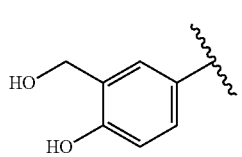

5. A compound or salt according to claim 4, wherein Y is —(CH$_2$)$_n$—, Z is OH and Q is a group of formula Q1:

Q1
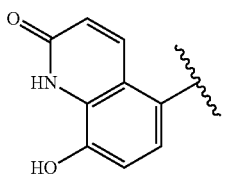

according to formula (IA):

(IA)
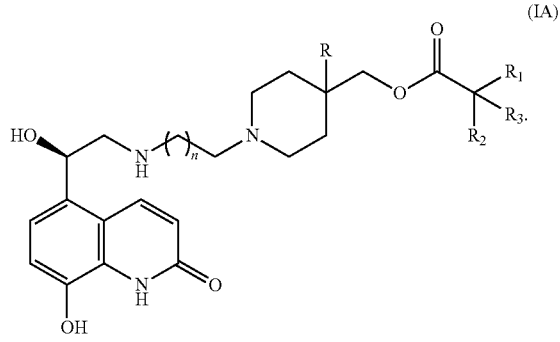

6. A compound or salt according to claim 5, wherein n is 4, 5, 6, 7 or 8.

7. A compound or salt according to claim 1, wherein Y is a divalent group of formula Y1:

Y1
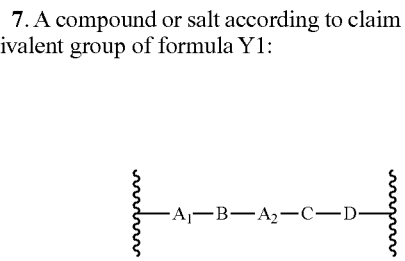

wherein A1 is (C$_3$-C$_8$)cycloalkylene, B and C are absent, D is (C$_1$-C$_{12}$)alkylene, Z is OH and Q is a group of formula Q1:

Q1
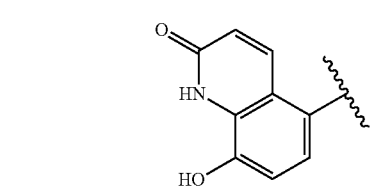

according to formula (IB), wherein (C$_3$-C$_8$)cycloalkylene is represented by "cy"

(IB)
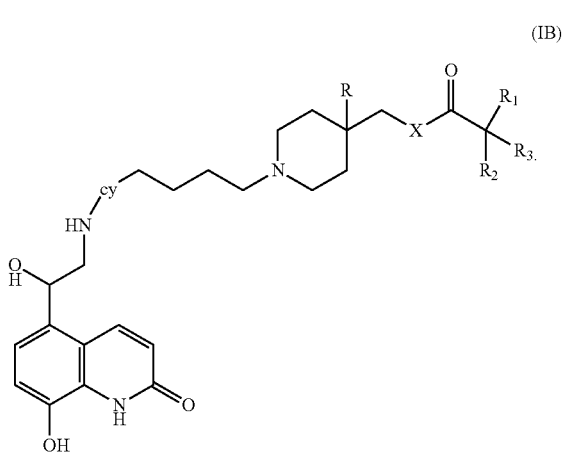

8. A compound or salt according to claim 4, wherein A1 is piperinyl and D is hexylene.

9. A compound or salt according to claim 1, wherein Y is —(CH$_2$)$_n$—, Z is H and Q is a group of formula Q3:

Q3
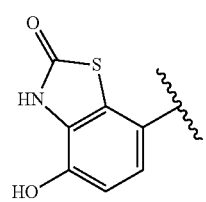

according to formula (IC):

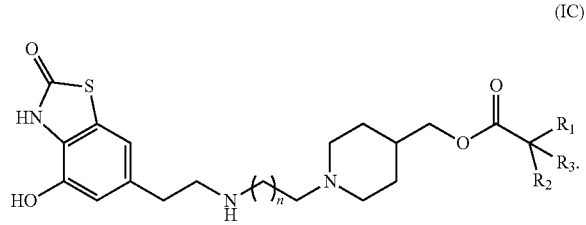

10. A compound or salt according to claim 9, wherein n is 8.

11. A pharmaceutical composition, comprising a compound or salt according to claim 1 and one or more pharmaceutically acceptable carriers and/or excipients.

12. A method for the treatment of a disease selected from the group consisting of asthma, chronic bronchitis, and chronic obstructive pulmonary disease, comprising administering an effective amount of a compound or salt according to claim 1 to a subject in need thereof.

13. A combination of a compound or salt according to claim 1 and one or more active ingredients selected from the group consisting of a corticosteroid, a P38 MAP kinase inhibitor, a IKK2 inhibitor, a HNE inhibitor, a PDE4 inhibitor, a leukotriene modulator, a NSAID, and a mucus regulator.

14. A pharmaceutical composition according to claim 11, which is in a form suitable to be administered by inhalation.

15. A pharmaceutical composition according to claim 14 which is an inhalable powder, a propellant-containing metering aerosol, or a propellant-free inhalable formulation.

16. A device comprising a pharmaceutical composition according to claim 14, which is a single- or multi-dose dry powder inhaler, a metered dose inhaler, or a soft mist nebulizer.

17. A method according to claim 12, wherein said disease is asthma.

18. A method according to claim 12, wherein said disease is chronic bronchitis.

19. A method according to claim 12, wherein said disease is chronic obstructive pulmonary disease.

* * * * *